(12) United States Patent
Suzuki et al.

(10) Patent No.: US 7,833,634 B2
(45) Date of Patent: Nov. 16, 2010

(54) 1,8-NAPHTHYRIDINE COMPOUND AND ORGANIC LIGHT-EMITTING DEVICE USING THE SAME

(75) Inventors: Koichi Suzuki, Yokohama (JP); Hiroshi Tanabe, Yokohama (JP); Chika Negishi, Yokosuka (JP); Taiki Watanabe, Akishima (JP); Akihiro Senoo, Kawasaki (JP); Kazunori Ueno, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 789 days.

(21) Appl. No.: 11/455,849

(22) Filed: Jun. 20, 2006

(65) Prior Publication Data

US 2006/0286408 A1 Dec. 21, 2006

(30) Foreign Application Priority Data

Jun. 21, 2005 (JP) ............................. 2005-180391

(51) Int. Cl.
*H01L 51/54* (2006.01)
*H05B 33/12* (2006.01)
*C07D 471/02* (2006.01)

(52) U.S. Cl. ...................... 428/690; 428/917; 313/504; 313/506; 257/E51.05; 546/122

(58) Field of Classification Search ................ 428/690; 546/122

See application file for complete search history.

(56) References Cited

U.S. PATENT DOCUMENTS

| | | | |
|---|---|---|---|
| 4,539,507 A | 9/1985 | VanSlyke et al. | 313/504 |
| 4,720,432 A | 1/1988 | VanSlyke et al. | 428/457 |
| 4,885,211 A | 12/1989 | Tang et al. | 428/457 |
| 5,393,614 A * | 2/1995 | Nakada | 428/690 |
| 6,492,557 B1 | 12/2002 | Ichimura et al. | 564/434 |
| 6,709,974 B2 | 3/2004 | Permana et al. | 438/633 |
| 6,727,379 B2 | 4/2004 | Ichimura et al. | 558/162 |
| 6,765,108 B2 | 7/2004 | Ichimura et al. | 558/411 |
| 6,774,257 B2 | 8/2004 | Ichimura et al. | 558/411 |
| 6,897,341 B2 | 5/2005 | Ichimura et al. | 564/433 |
| 6,972,334 B1 | 12/2005 | Shibanuma et al. | 546/88 |
| 7,049,470 B1 | 5/2006 | Ichimura et al. | 564/427 |
| 7,087,310 B2 | 8/2006 | Ichimura et al. | 428/457 |
| 7,186,469 B2 | 3/2007 | Shibanuma et al. | 428/690 |
| 7,196,225 B2 | 3/2007 | Ichimura et al. | 564/427 |
| 2002/0096995 A1* | 7/2002 | Mishima et al. | 313/506 |
| 2002/0135292 A1* | 9/2002 | Kamatani et al. | 313/483 |
| 2002/0146590 A1* | 10/2002 | Matsuo et al. | 428/690 |
| 2003/0091861 A1* | 5/2003 | Okada et al. | 428/690 |
| 2005/0052133 A1 | 3/2005 | Ichimura et al. | 313/510 |
| 2005/0073641 A1 | 4/2005 | Shibanuma et al. | 349/182 |
| 2005/0146268 A1* | 7/2005 | Seo et al. | 313/506 |
| 2005/0154208 A1 | 7/2005 | Shibanuma et al. | 546/88 |
| 2006/0017050 A1 | 1/2006 | Hasegawa et al. | 257/40 |
| 2006/0097227 A1* | 5/2006 | Okajima et al. | 252/301.16 |
| 2008/0116789 A1* | 5/2008 | Yamaguchi et al. | 313/504 |

FOREIGN PATENT DOCUMENTS

| | | |
|---|---|---|
| JP | 02-216791 | 8/1990 |
| JP | 05-331459 | 12/1993 |
| JP | 07-082551 | 3/1995 |
| JP | 10-233284 | 9/1998 |
| JP | 2001-131174 | 5/2001 |
| JP | 2001-267080 | 9/2001 |
| WO | WO 2004026870 A1 * | 4/2004 |

OTHER PUBLICATIONS

Anne Petitjean, Jean-Marie Lehn, Richard G. Khoury, Andre De Cian, and Nathalie Kyritsadas. "Synthesis, characterisation and properties of a crescent-shaped tetranuclear bis-dirhodium complex." Comptes Rendus Chimie. 2002, vol. 5, Issue 4, pp. 337-340.*
Juana Gajardo, Juan C. Araya, Sergio A. Moya, Alvaro J. Pardey, Veronique Guerchais, Hubert Le Bozec, and Pedro Aguirre. "New polynuclear carbonyl ruthenium(II) complexes derived from 1,8-naphthyridine." Applied Organometallic Chemistry. 2006, vol. 20, Issue 4, pp. 272-276.*
Newkome et al., "Chemistry of Heterocyclic Compounds. 61. Synthesis and Conformational Studies of Macrocycles Possessing 1,8- or 1,5-Naphthyridino Subunits Connected by Carbon-Oxygen Bridges," *J. Org. Chem.*, vol. 46, No. 5, 834-839 (1981).
van der Plas et al., "On the Bromination of 1,7- and 1,8-Naphthyridine in Nitrobenzene," *J. Heterocyclic Chem.*, vol. 13, No. 5, 961-965, (1976).
Weissenfels et al., "On the Reaction of 1,8-Naphthyridene with Organolithium," *Z. Chem.*, vol. 18, 382-383 (1978).
Miyaura et al., "Palladium-Catalyzed Cross-Coupling reactions of Organoboron Compounds," *Chem Rev.*, vol. 95, No. 7, 1-41 (1995).

* cited by examiner

*Primary Examiner*—D. Lawrence Tarazano
*Assistant Examiner*—Andrew K Bohaty
(74) *Attorney, Agent, or Firm*—Fitzpatrick, Cella, Harper & Scinto

(57) ABSTRACT

Provided a novel 1,8-naphthyridine compound represented by the following general formula [I]:

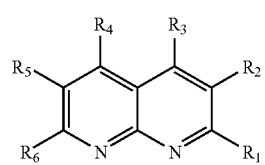

[I]

wherein $R_1$ to $R_6$ each represent a hydrogen atom; an alkyl group, a halogen atom; a trifluoromethyl group; and a cyano group, and may be the same as or different from one another, and that at least two of $R_1$ to $R_6$ each represent an aralkyl group, an aryl group, a heterocyclic group, a condensed polycyclic aromatic group, a condensed polycyclic heterocyclic group and an aryloxy group which may be substituted; and a substituted amino group. The 1,8-naphthyridine is employed in an organic compound layer provided between a pair of electrodes in an organic light-emitting device.

10 Claims, 3 Drawing Sheets

US 7,833,634 B2

1,8-NAPHTHYRIDINE COMPOUND AND ORGANIC LIGHT-EMITTING DEVICE USING THE SAME

BACKGROUND OF THE INVENTION

1. Field of the Invention

The present invention relates to a novel organic compound and an organic light-emitting device using the same.

2. Related Background Art

An organic light-emitting device includes an anode, a cathode, and a thin film containing a fluorescent organic compound or a phosphorescent organic compound, which is sandwiched between the anode and the cathode. An electron and a hole are injected from the respective electrodes, whereby an exciton of the fluorescent compound or the phosphorescent compound is generated. The device utilizes light radiated when the exciton returns to its ground state.

The recent progress of an organic light-emitting device is significant, and suggests that the device can be used in wide applications because of making it possible to form a thin, light-weight organic light-emitting device having a high luminance at a low applied voltage, a variety of emission wavelengths, and high-speed responsiveness. However, at present, improvements in initial characteristics such as a luminous efficiency, and duration characteristics such as a duration against luminance degradation due to long-term light emission have been needed. Those initial characteristics and duration characteristics result from all layers for forming the device, including a hole injection layer, a hole transport layer, a light emission layer, a hole blocking layer, an electron transport layer, an electron injection layer, and the like.

Examples of conventionally known materials to be used in the hole blocking layer, the electron transport layer, and the electron injection layer include phenanthroline compounds, aluminum quinolinol complexes, oxadiazole compounds, and triazole compounds. For example, in each of Japanese Patent Application Laid-open Nos. H05-331459, H07-082551, 2001-267080, 2001-131174, H02-216791 and H10-233284, and U.S. Pat. Nos. 4,539,507, 4,720,432 and 4,885,211, each of the above materials is used in a light emission layer or an electron transport layer. However, the initial characteristics and duration characteristics of an organic light-emitting device of each of those documents are not sufficient.

An object of the present invention is to provide a novel 1,8-naphthyridine compound.

Another object of the present invention is to provide an organic light-emitting device having a high emission luminance and a high emission efficiency by using the novel 1,8-naphthyridine compound. Another object of the present invention is to provide an organic light-emitting device having high durability and showing small degradation of luminance due to long-term light emission.

Further another object of the present invention is to provide an organic light-emitting device that can be easily produced at a relatively low cost.

SUMMARY OF THE INVENTION

That is, a 1,8-naphthyridine compound of the present invention is represented by the following general formulae [I] to [III]:

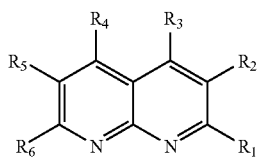

[I]

wherein $R_1$ to $R_6$ each represent one selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, a trifluoromethyl group, and a cyano group, and $R_1$ to $R_6$ may be the same as or different from one another, provided that at least two of $R_1$ to $R_6$ each represent one selected from the group consisting of a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, and a substituted amino group;

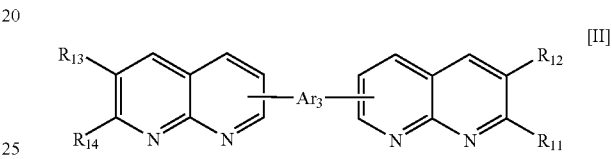

[II]

wherein $R_{11}$ to $R_{14}$ each represent one selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, a trifluoromethyl group, and a cyano group, and $R_{11}$ to $R_{14}$ may be the same as or different from one another; and $Ar_3$ represents one selected from the group consisting of a divalent, substituted or unsubstituted aromatic group, a divalent, substituted or unsubstituted heterocyclic group, a divalent, substituted or unsubstituted condensed polycyclic aromatic group, and a divalent, substituted or unsubstituted condensed polycyclic heterocyclic group;

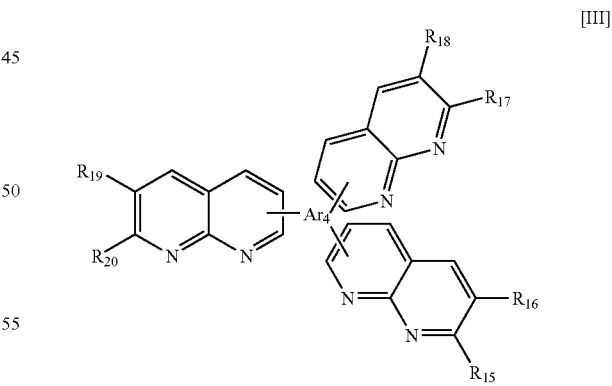

[III]

wherein $R_{15}$ to $R_{20}$ each represent one selected from the group consisting of a hydrogen atom, a substituted or unsubstituted alkyl group, a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, a substituted amino group, a halogen atom, a trifluoromethyl group, and a cyano group, and $R_{15}$ to $R_{20}$ may be the same as or different from one another; and; $Ar_4$ represents one selected from the group consisting of a trivalent, substituted or unsubstituted aromatic group, a trivalent, substituted or unsubstituted heterocyclic group, a trivalent, substituted or unsubstituted condensed polycyclic aromatic group, and a trivalent, substituted or unsubstituted condensed polycyclic heterocyclic group.

An organic light-emitting device of the present invention includes at least: a pair of electrodes composed of an anode and a cathode; and one or more layers each containing an organic compound, the layers being interposed between the pair of electrodes, wherein at least one layer of the layers each containing the organic compound contains at least one kind of the 1,8-naphthyridine compound.

An organic light-emitting device using the 1,8-naphthyridine compound of the present invention provides light emission having a high luminance at a low applied voltage, and is excellent in durability. In particular, an organic layer containing the 1,8-naphthyridine compound of the present invention is excellent as an electron transport layer and as the light emission layer.

Furthermore, the device can be produced by a vacuum deposition method, a casting method, or the like. The device having a large area can be easily produced at a relatively low cost.

DESCRIPTION OF THE PREFERRED EMBODIMENTS

Figure 1:
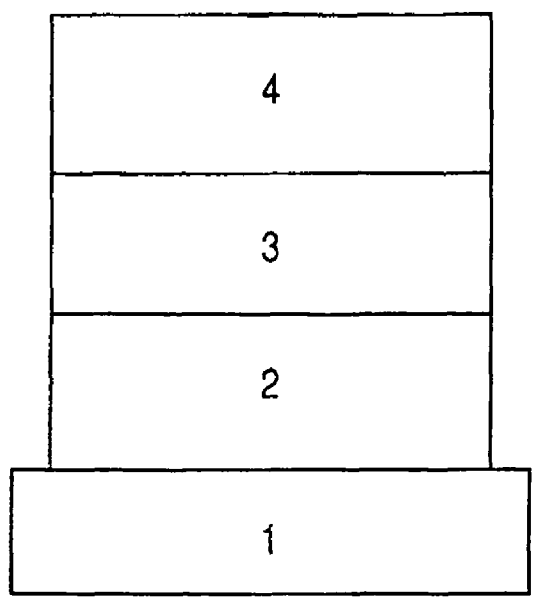
FIG. 1 is a sectional view showing an example of an organic light-emitting device according to the present invention.

Hereinafter, the present invention will be described in detail.

First, a 1,8-naphthyridine compound of the present invention will be described.

The 1,8-naphthyridine compound of the present invention is represented by any one of the above-described general formulae [I] to [III].

The 1,8-naphthyridine compound represented by the general formula [I] is preferably a compound in which $R_2$ to $R_5$ each represent one selected from a hydrogen atom, a substituted or unsubstituted alkyl group, a halogen atom, a trifluoromethyl group, and a cyano group, and $R_1$ and $R_6$ each represent a group selected from a substituted or unsubstituted aralkyl group, a substituted or unsubstituted aryl group, a substituted or unsubstituted heterocyclic group, a substituted or unsubstituted condensed polycyclic aromatic group, a substituted or unsubstituted condensed polycyclic heterocyclic group, a substituted or unsubstituted aryloxy group, and a substituted amino group.

Specific examples of the substituents in the general formulae [I] to [III] will be shown below.

The alkyl group includes methyl, ethyl, n-propyl, iso-propyl, n-butyl, ter-butyl, octyl, and the like.

The aralkyl group includes benzyl, phenethyl, and the like.

The aryl group includes phenyl, biphenyl, terphenyl, and the like.

The heterocyclic group includes thienyl, pyrrolyl, pyridyl, bipyridyl, terpyridyl, oxazolyl, oxadiazolyl, thiazolyl, thiadiazolyl, and the like.

The condensed polycyclic aromatic group includes fluorenyl, naphthyl, fluoranthenyl, anthryl, phenanthryl, pyrenyl, tetracenyl, pentacenyl, perylenyl, triphenylenyl, and the like.

The condensed polycyclic heterocyclic group includes quinolyl, carbazolyl, acridinyl, phenazyl, phenanthrolyl, and the like.

The aryloxy group includes phenoxyl, fluorenoxyl, naphthoxyl, and the like.

The substituted amino group includes dimethylamino, diethylamino, dibenzylamino, diphenylamino, ditolylamino, dianisolylamino, fluorenylphenylamino, difluorenyl, naphthylphenylamino, dinaphthylamino, and the like.

The halogen atom includes fluorine, chlorine, bromine, iodine, and the like.

The divalent or trivalent aromatic group, heterocyclic group, condensed polycyclic aromatic group, and condensed polycyclic heterocyclic group include the above-mentioned aryl group, heterocyclic group, condensed polycyclic aromatic group, condensed polycyclic heterocyclic group and the like which are modified to have divalence or trivalence.

Substituents which the above-mentioned substituents may have include alkyl groups such as methyl, ethyl, n-propyl, iso-propyl, n-butyl, ter-butyl and octyl; aralkyl groups such as benzyl and phenethyl; aryl groups such as phenyl, biphenyl and terphenyl; heterocyclic groups such as thienyl, pyrrolyl, pyridyl, bipyridyl, terpyridyl, oxazolyl, oxadiazolyl, thiazolyl and thiadiazolyl; condensed polycyclic aromatic groups such as fluorenyl, naphthyl, fluoranthenyl, anthryl, phenanthryl, pyrenyl, tetracenyl, pentacenyl, perylenyl and triphenylenyl; condensed polycyclic heterocyclic groups such as quinolyl, carbazolyl, acridinyl, phenazyl and phenanthrolyl; aryloxy groups such as phenoxyl, fluorenoxyl and naphthoxyl; substituted amino groups such as dimethylamino, diethylamino, dibenzylamino, diphenylamino, ditolylamino, dianisolylamino, fluorenylphenylamino, difluorenyl, naphthylphenylamino and dinaphthylamino; halogen atoms such as fluorine, chlorine, bromine and iodine; trifluoromethyl; cyano; and the like.

Next, representative examples of the 1,8-naphthyridine compound of the present invention will be shown below. However, the present invention is not limited to these examples.

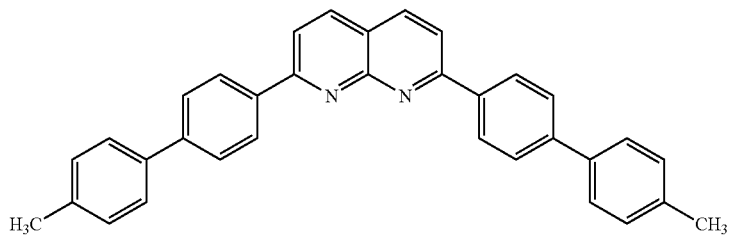
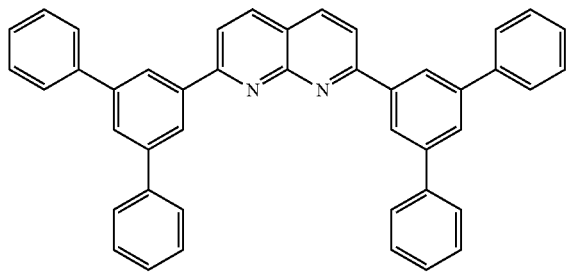
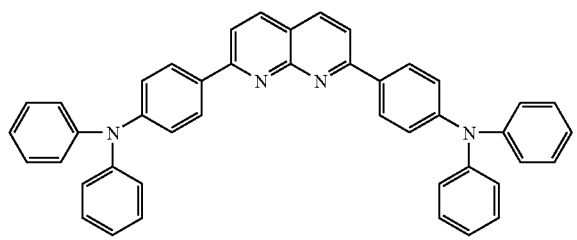
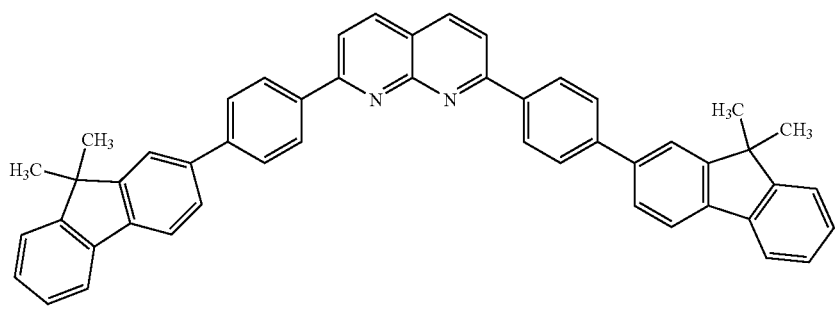
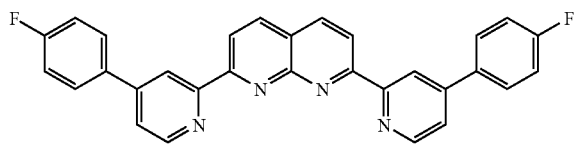
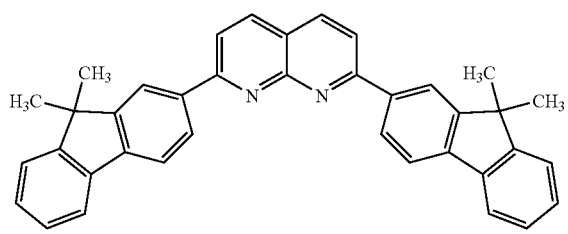

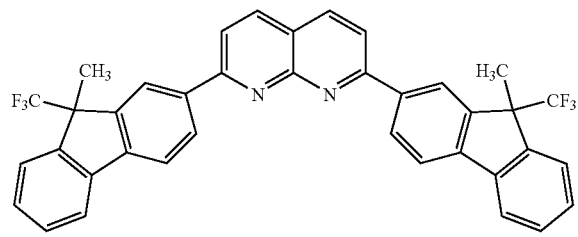
7
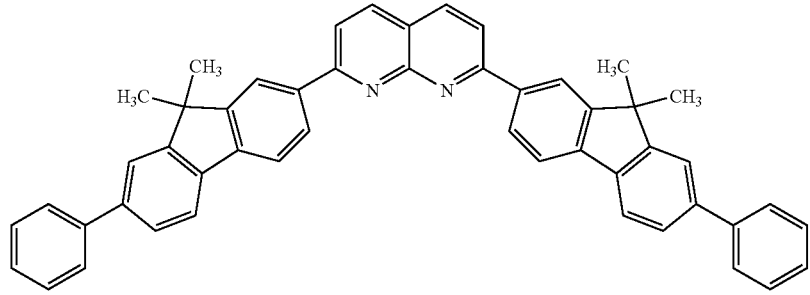
8
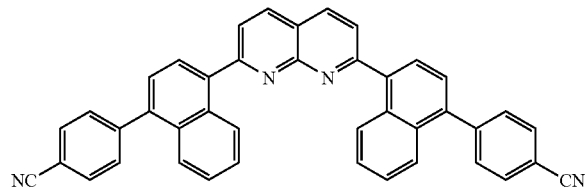
9
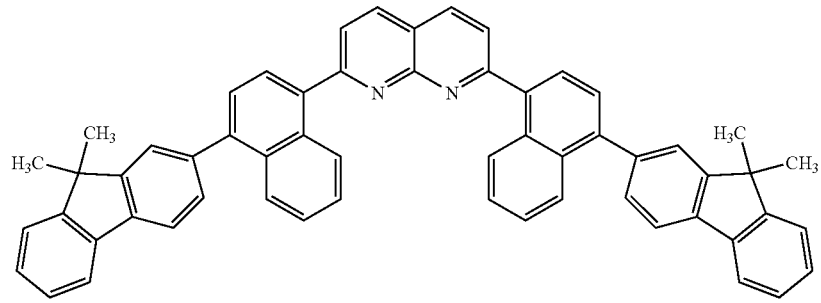
10
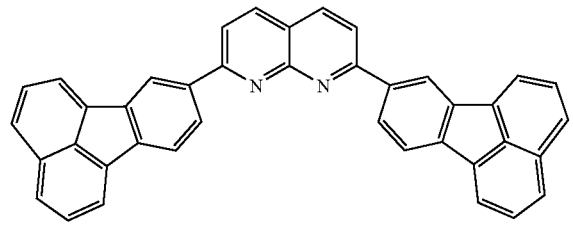
11
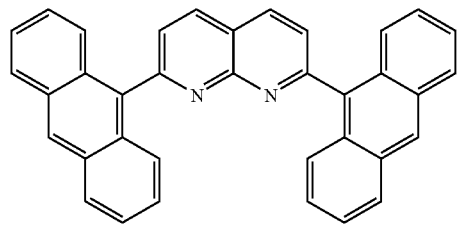
12
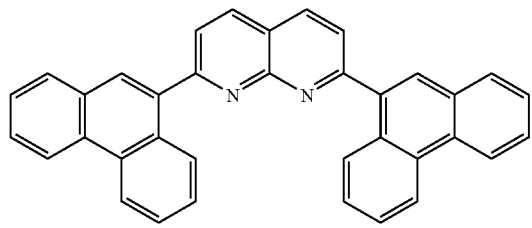
13

-continued
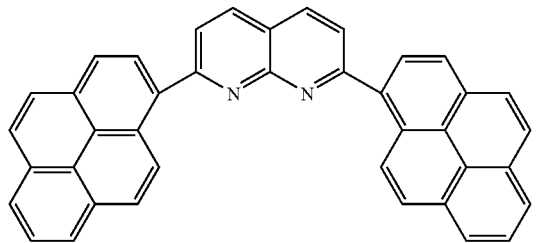
14
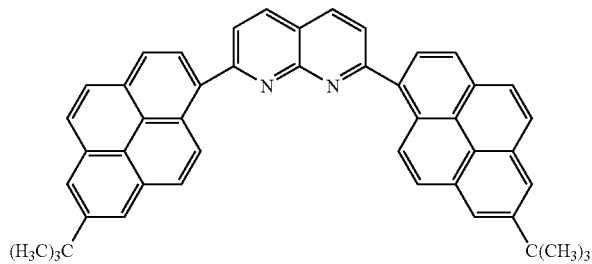
15
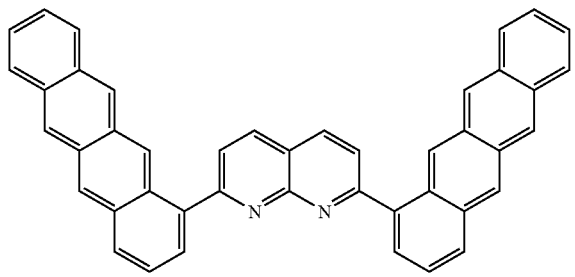
16
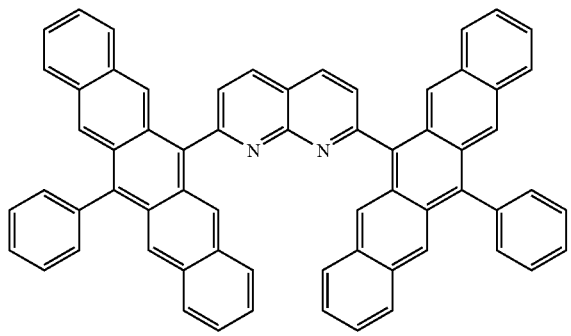
17
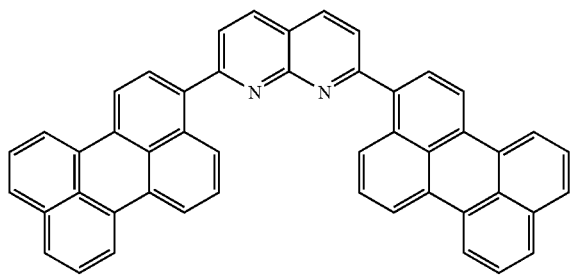
18

-continued
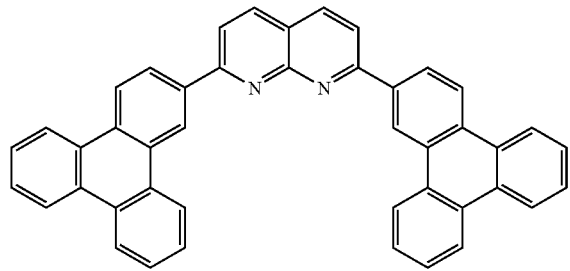
19
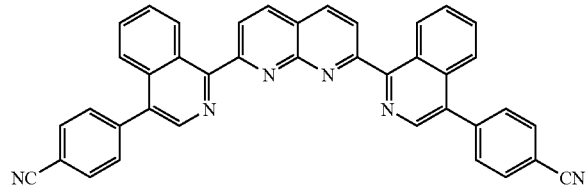
20
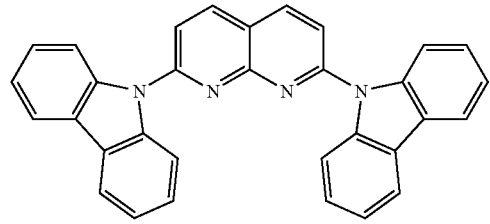
21
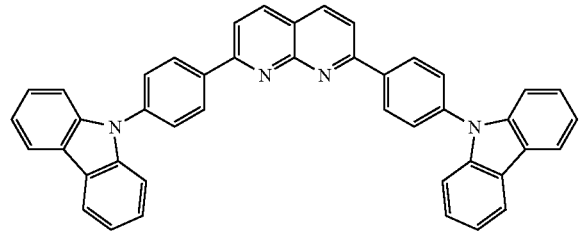
22
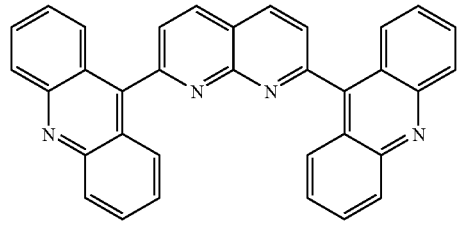
23
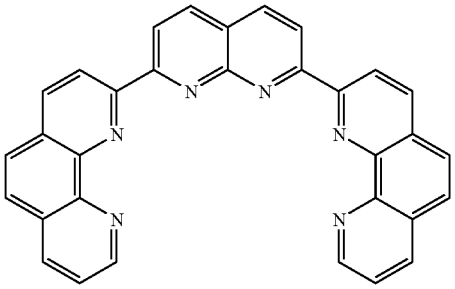
24
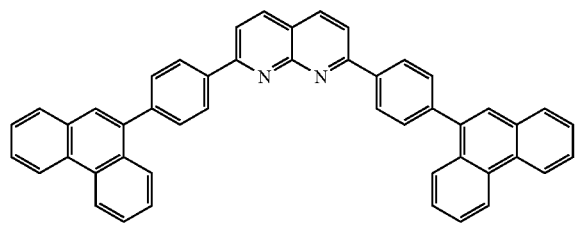
25

-continued
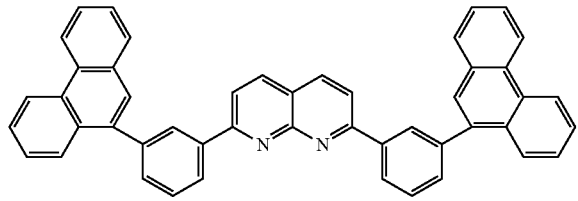
26
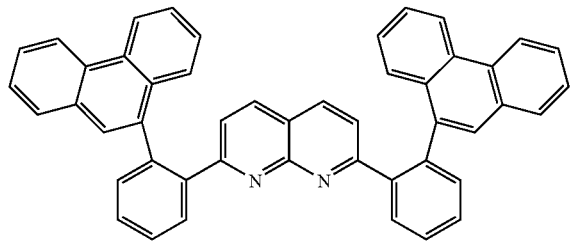
27
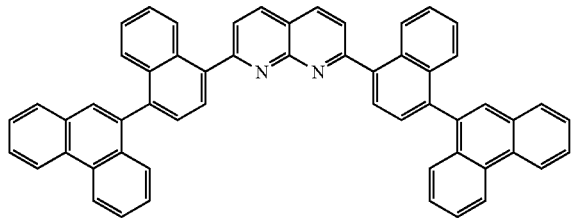
28
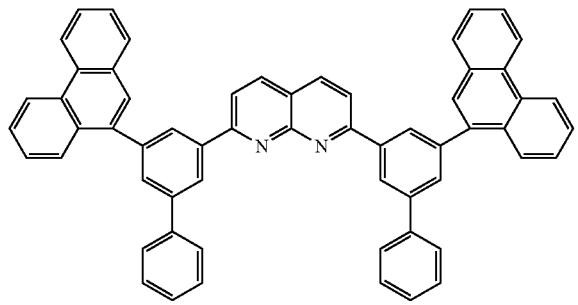
29
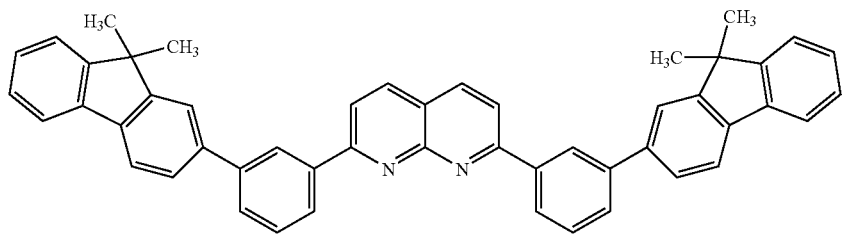
30
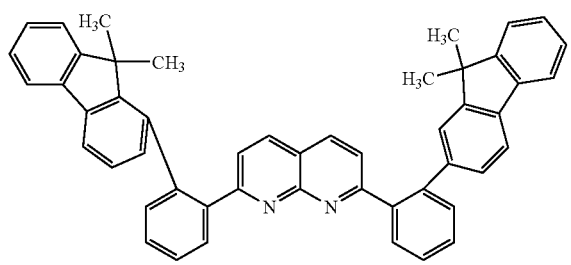
31

-continued
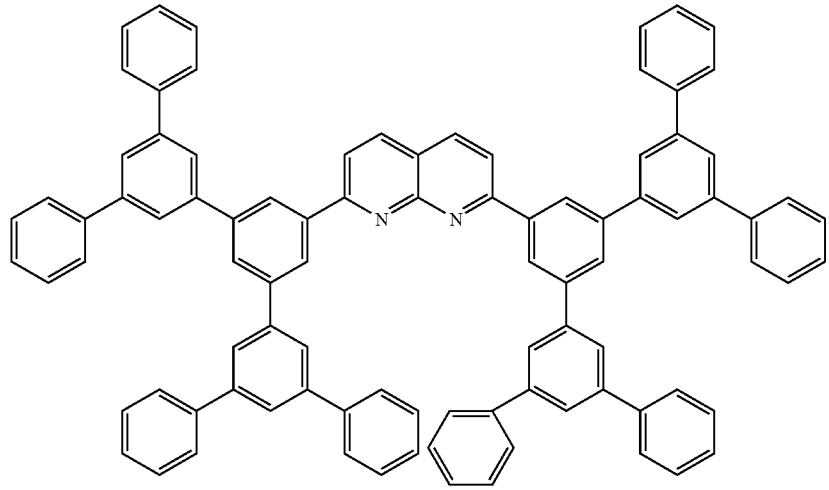
32
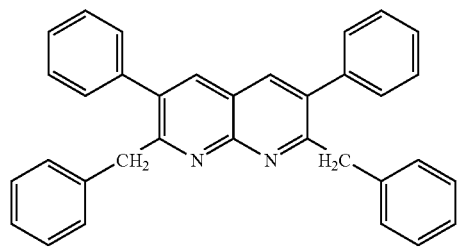
33
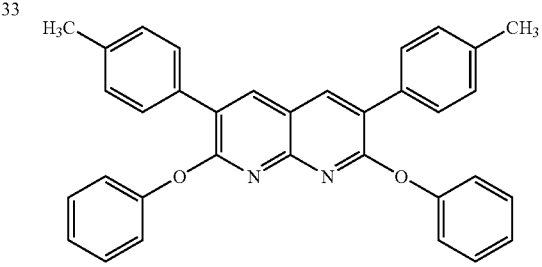
34
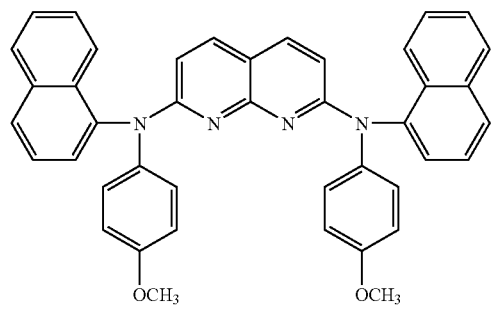
35
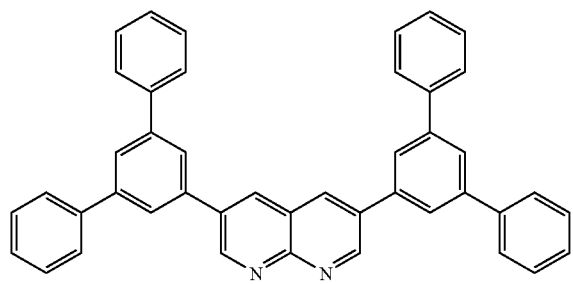
36

-continued
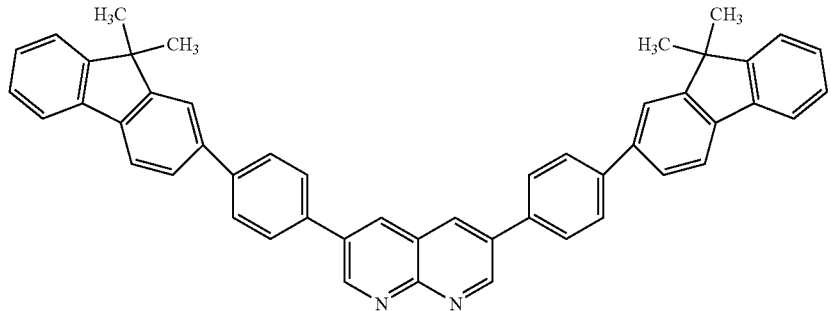
37
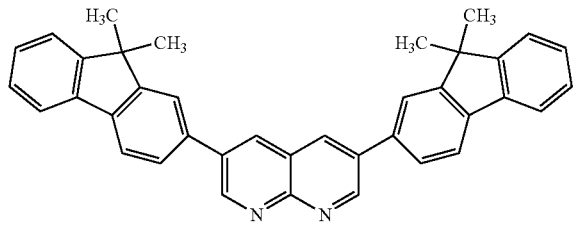
38
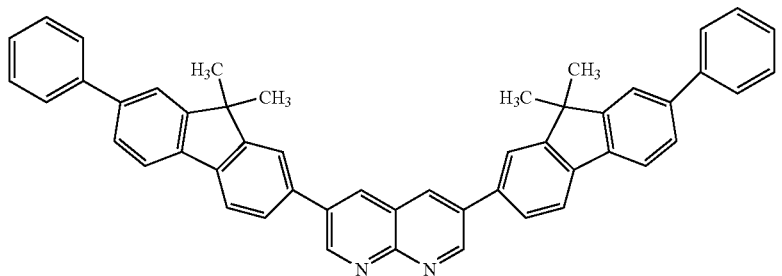
39
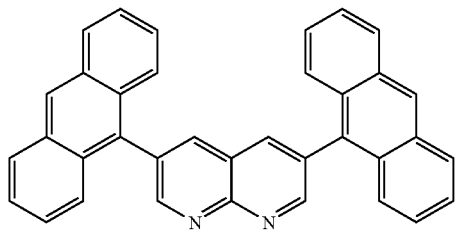
40
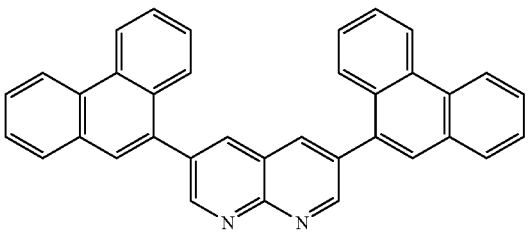
41
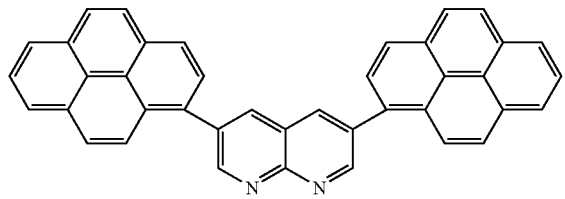
42
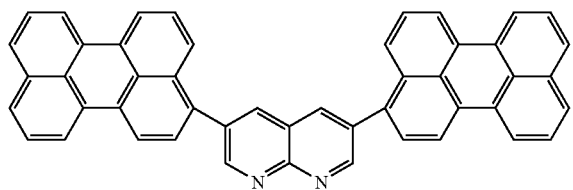
43

-continued
44
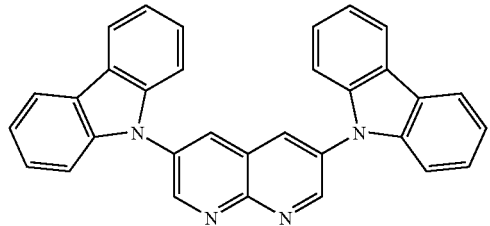
45
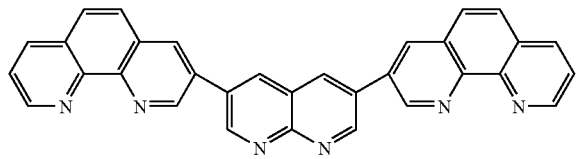
46
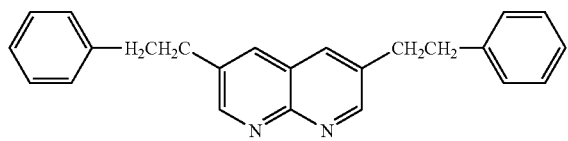
47
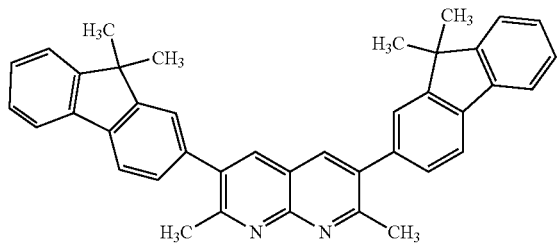
48
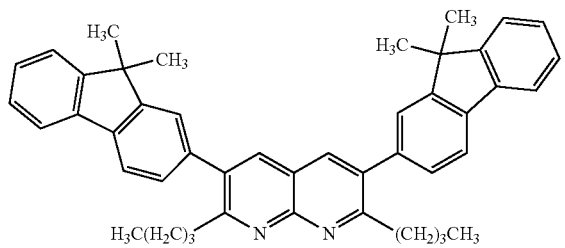
49
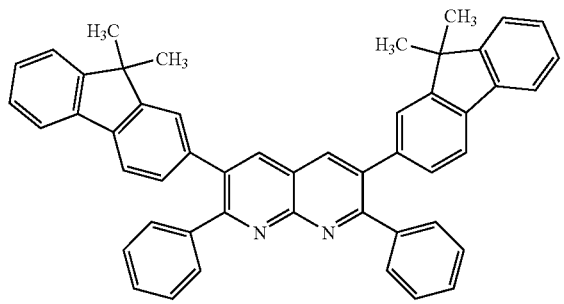

-continued
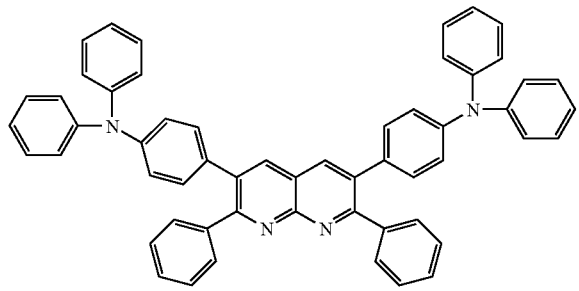
50
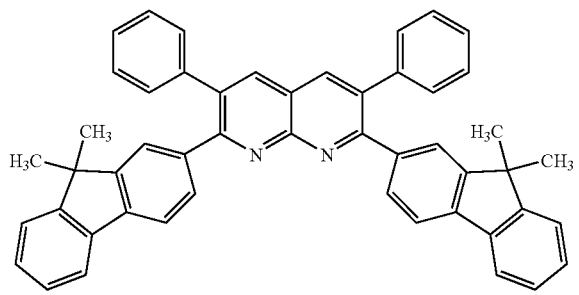
51
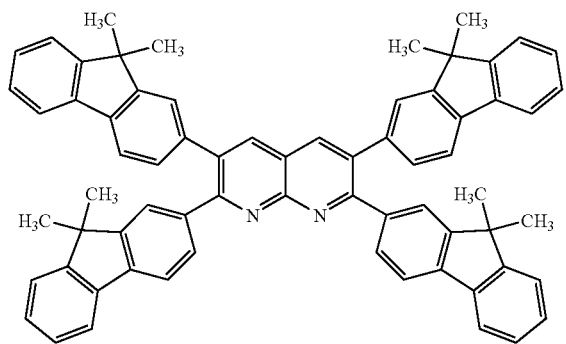
52
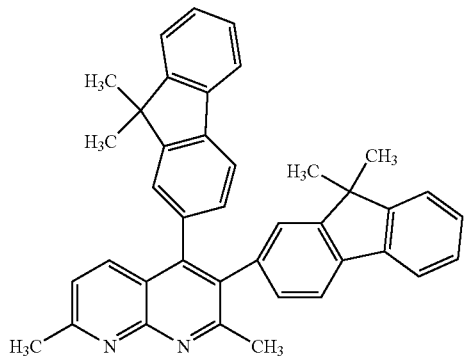
53

-continued
54
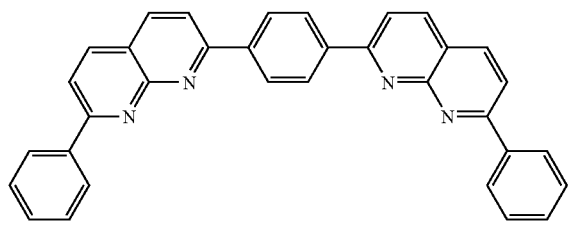
55
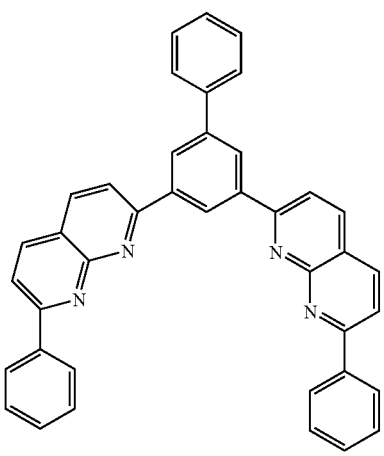
56
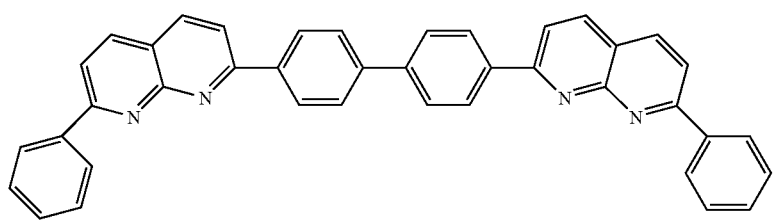
57
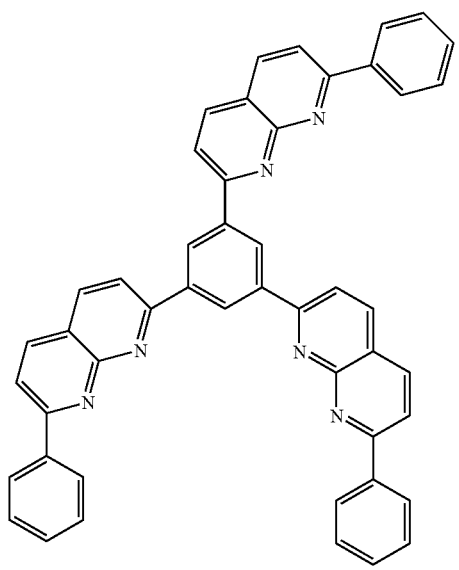
58
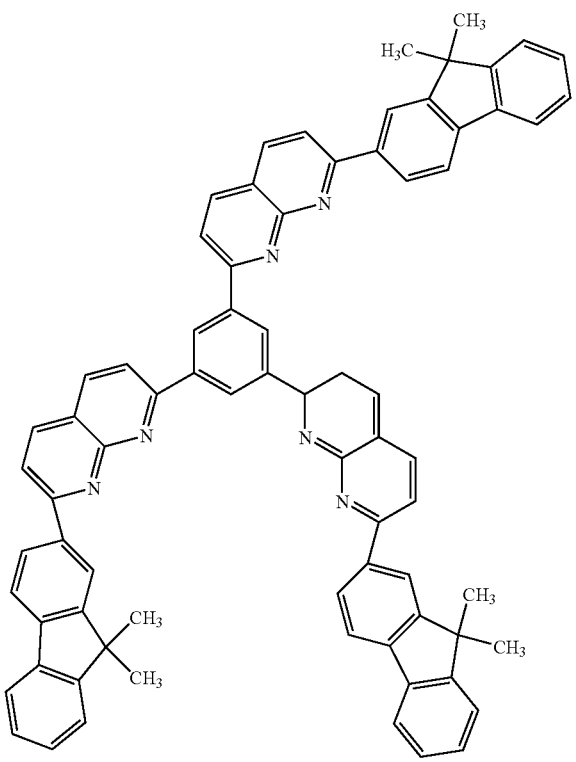

-continued
59
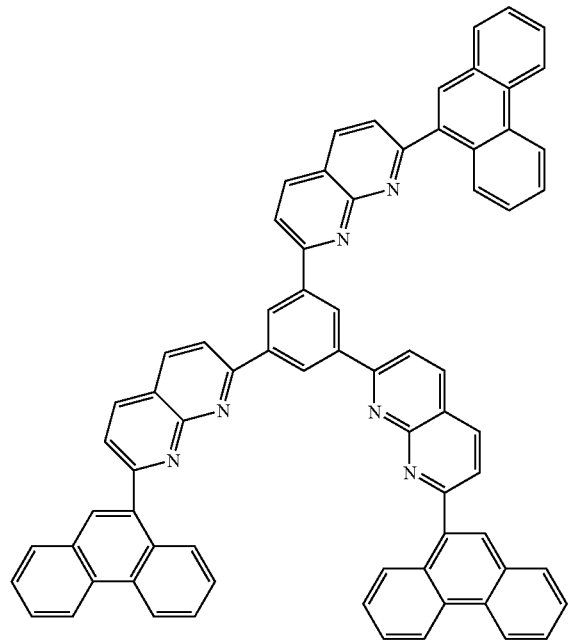
60
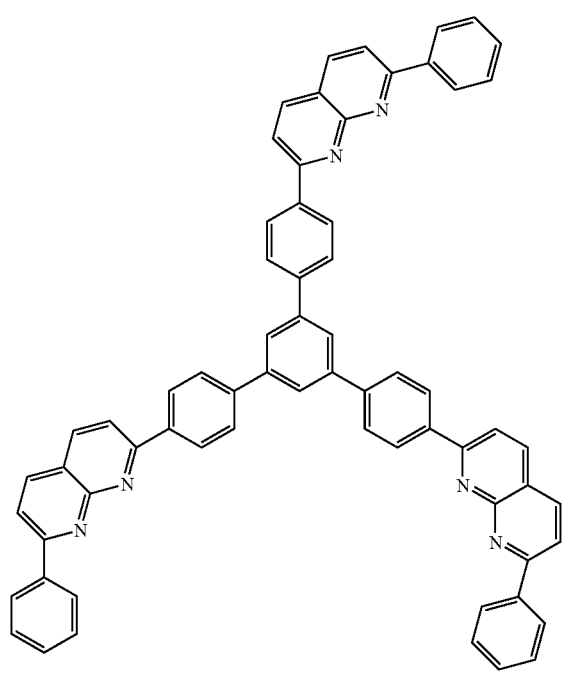

The 1,8-naphthyridine compound of the present invention can be synthesized by means of a generally known method. Examples of the method include methods described in J. Org. Chem., 46, 833 (1981), J. Heterocycl. Chem., 13, 961 (1976), and Z. Chem. 18, 382 (1978). A 1,8-naphthyridine compound intermediate is produced by means of any one of those methods. Furthermore, the 1,8-naphthyridine compound can be produced from the above intermediate by means of a synthesis method such as a Suzuki Coupling method using a palladium catalyst (see, for example, Chem. Rev., 95, 2457, (1995)).

The 1,8-naphthyridine compound of the present invention is superior to a conventional compound in electron-transporting property, light-emitting property, and durability. In addition, the 1,8-naphthyridine compound is useful as a layer containing an organic compound of an organic light-emitting device, in particular, an electron transport layer or a light emission layer. In addition, a layer formed of the 1,8-naphthyridine compound by means of a vacuum deposition method, a solution application method, or the like hardly causes crystallization or the like, and is excellent in stability with the elapse of time. In particular, a compound having a relatively low HOMO among the 1,8-naphthyridine compounds of the present invention has high hole-blocking property, and is particularly preferable as a hole blocking layer or an electron transport layer.

Next, an organic light-emitting device of the present invention will be described in detail.

An organic light-emitting device of the present invention includes at least: a pair of electrodes composed of an anode and a cathode; and one or more layers each containing an organic compound, the layers being interposed between the pair of electrodes, in which at least one layer of the layers each containing the organic compound contains at least one kind of the 1,8-naphthyridine compound according to the present invention.

In an organic light-emitting device of the present invention, the layer containing at least one kind of the 1,8-naphthyridine compound preferably is one of a hole blocking layer, an electron transport layer, a light emission layer, and an electron injection layer.

In the organic light-emitting device of the present invention, the layer containing at least the 1,8-naphthyridine compound of the present invention can be formed between the anode and the cathode by means of a vacuum deposition method or a solution application method. The thickness of the organic layer is thinner than 10 μm, and the layer is formed into a thin film having a thickness of preferably 0.5 μm or less, or more preferably 0.01 to 0.5 μm.

FIGS. 1, 2, 3, 4, 5 and 6 show preferable examples of the organic light-emitting device of the present invention.

Reference numerals of the respective drawings will be described.

Reference numeral 1 denotes a substrate; 2, an anode; 3, a light emission layer; 4, a cathode; 5, a hole transport layer; 6, an electron transport layer; 7, a hole injection layer; and 8, a hole/exciton blocking layer.

FIG. 1 is a sectional view showing an example of the organic light-emitting device of the present invention. FIG. 1 shows a constitution in which the anode 2, the light emission layer 3, and the cathode 4 are sequentially provided on the substrate 1 in mentioned order. The light-emitting device to be used in this example is useful for the case where the device itself has a single compound with a hole-transporting ability, an electron-transporting ability, and light-emitting property or the case where compounds having the respective properties are used as a mixture.

Figure 2:
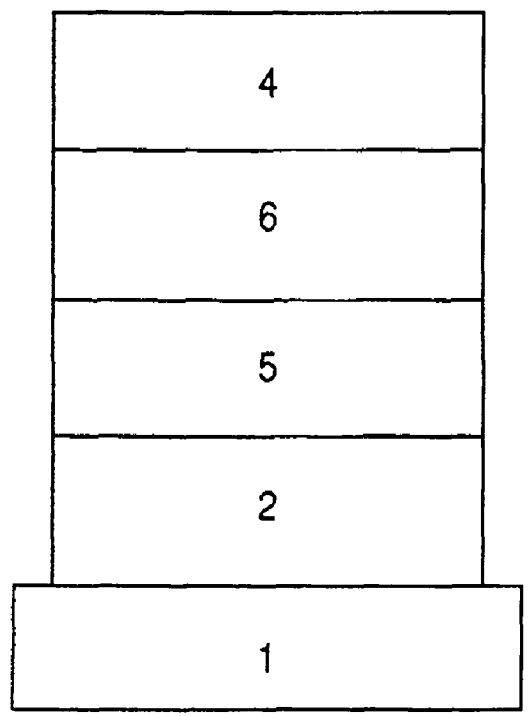
FIG. 2 is a sectional view showing another example of the organic light-emitting device according to the present invention.

FIG. 2 is a sectional view showing another example of the organic light-emitting device of the present invention. FIG. 2 shows a constitution in which the anode 2, the hole transport layer 5, the electron transport layer 6, and the cathode 4 are sequentially provided on the substrate 1. In this case, a material having one or both of hole-transporting property and electron-transporting property is used as a luminescent substance in each layer. This case is useful when the device is used in combination with a mere hole-transporting substance or electron-transporting substance having no light-emitting property. In addition, in this case, a light emission layer is composed of the hole transport layer 5 or the electron transport layer 6.

Figure 3:
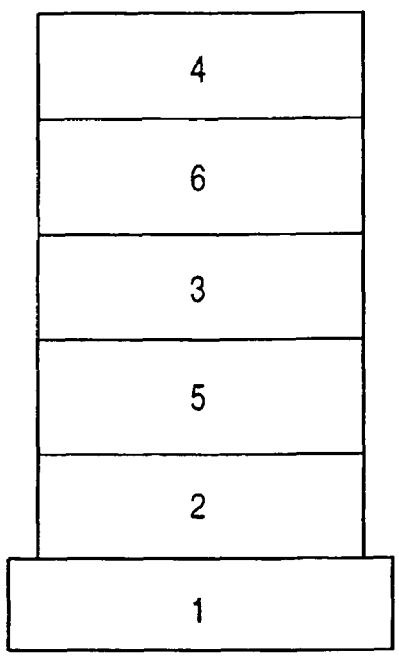
FIG. 3 is a sectional view showing further another example of the organic light-emitting device according to the present invention.

FIG. 3 is a sectional view showing another example of the organic light-emitting device of the present invention. FIG. 3 shows a constitution in which the anode 2, the hole transport layer 5, the light emission layer 3, the electron transport layer 6, and the cathode 4 are sequentially provided on the substrate 1. This constitution separates a carrier-transporting function and a light-emitting function. In addition, the device is timely used in combination with compounds having respective properties such as hole-transporting property, electron-transporting property, and light-emitting property, so that the degree of freedom in selection of materials extremely increases. In addition, various compounds different from each other in emission wavelength can be used. As a result, the range of luminescent colors can be widened. Furthermore, an emission efficiency can be improved by effectively confining each carrier or exciton in the central light emission layer 3.

Figure 4:
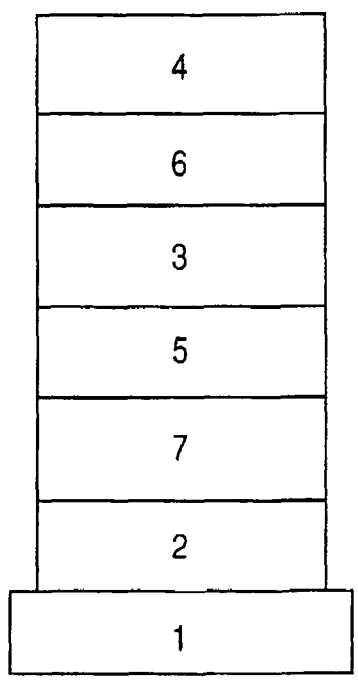
FIG. 4 is a sectional view showing still further another example of the organic light-emitting device according to the present invention.

FIG. 4 is a sectional view showing another example of the organic light-emitting device of the present invention. FIG. 4 shows the same constitution as that of FIG. 3 except that the hole injection layer 7 is inserted on the side of the anode 2. This constitution has an improved effect on adhesiveness between the anode 2 and the hole transport layer 5 or on hole-injecting property, and is effective in lowering voltage.

Figure 5:
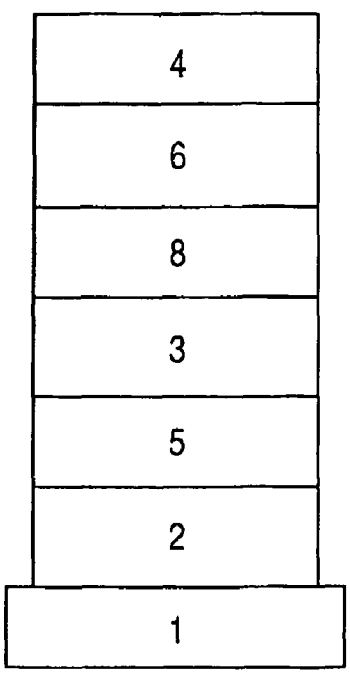
FIG. 5 is a sectional view showing still further another example of the organic light-emitting device according to the present invention.
Figure 6:
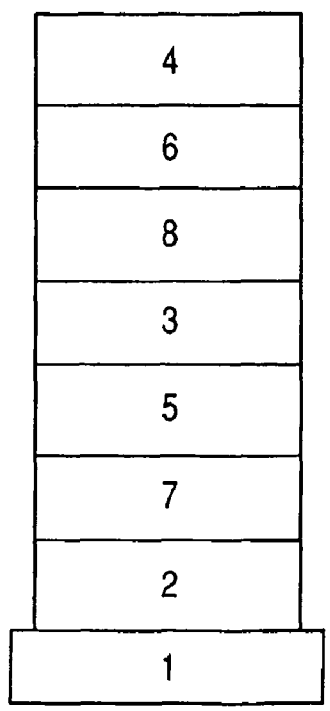
FIG. 6 is a sectional view showing still further another example of the organic light-emitting device according to the present invention.

FIGS. 5 and 6 are sectional views each showing another example of the organic light-emitting device of the present invention. FIGS. 5 and 6 are different from FIGS. 3 and 4 in that a layer for inhibiting the passing of a hole or an exciton to the side of the cathode (hole/exciton blocking layer 8) is added. In each of those figures, the device is constituted in such a manner that the hole/exciton blocking layer is inserted into a gap between the light emission layer 3 and the electron transport layer 6. In this constitution, the use of a compound having an extremely high ionization potential in the hole/exciton blocking layer 8 is effective in improving an emission efficiency.

It should be noted that the device constitutions shown in FIGS. 1, 2, 3, 4, 5 and 6 are merely very basic constitutions, and the constitution of an organic light-emitting device using the compound of the present invention is not limited to these constitutions. The device may adopt any one of various layer constitutions. For example, an insulating layer may be provided to an interface between an electrode and an organic layer. Alternatively, an adhesive layer or an interference layer may be provided. Alternatively, a hole transport layer may be composed of two layers different from each other in ionization potential.

The 1,8-naphthyridine compound of the present invention is superior to a conventional compound in electron-transporting property, light-emitting property, and durability, and can be used in any one of the constitutions shown in FIGS. 1, 2, 3, 4, 5 and 6.

The organic light-emitting device of the present invention uses the 1,8-naphthyridine compound of the present invention preferably as a component for its electron transport layer or its light emission layer. In addition, the device can use a conventionally known hole-transporting compound, light-emitting compound, electron-transporting compound, or the like together with the compound of the present invention as required.

Examples of those compounds will be given below.

Hole-Transporting Compound

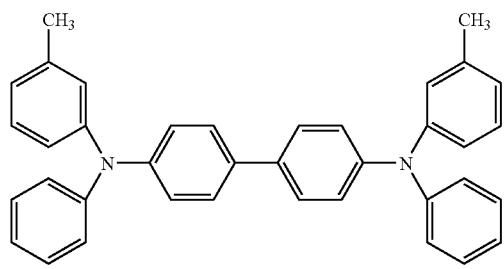

TPD

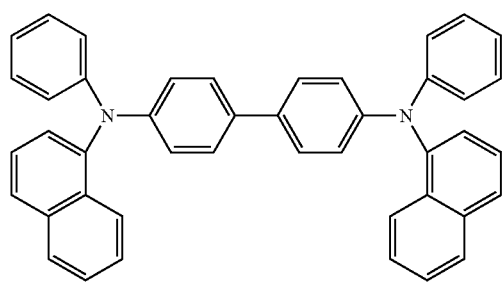

α-NPD

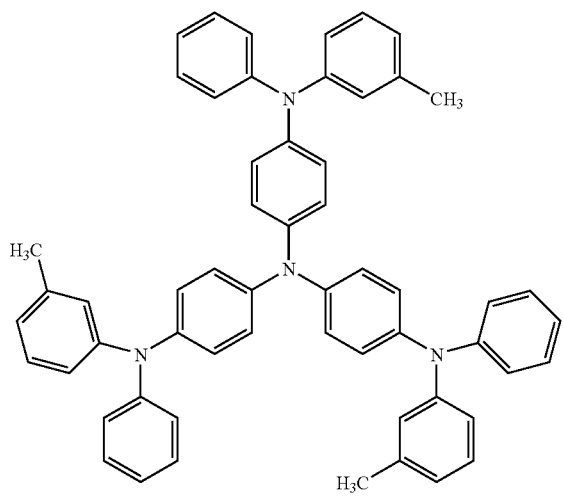

m-MTDATA

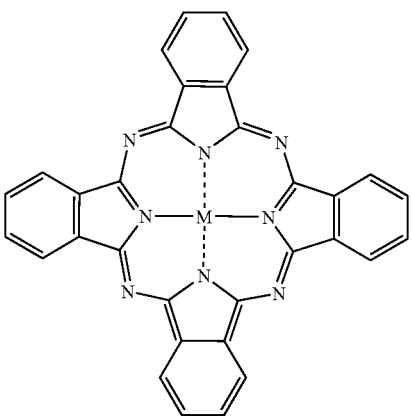

Met: Cu, Md, AlCl, TiO, SiCl$_2$, etc
Met-Pc

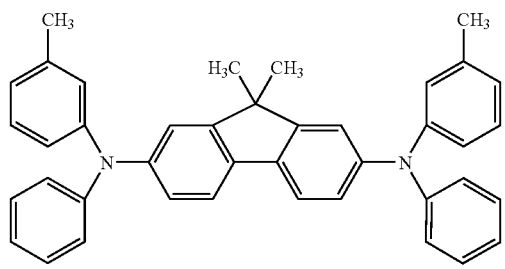

DTDPFL

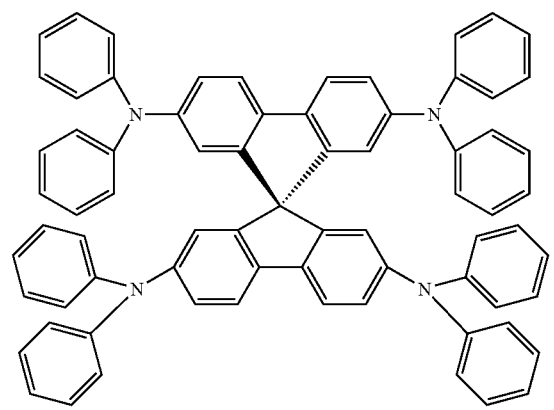

spiro-TPD

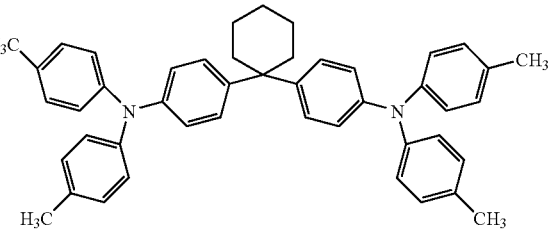

TPAC

-continued
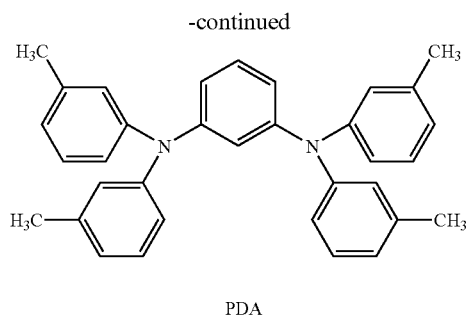
PDA
Electron-Transporting Luminescent Material
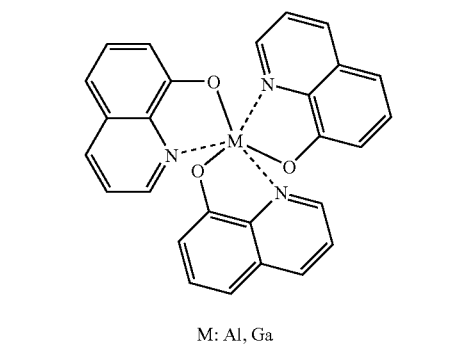
M: Al, Ga
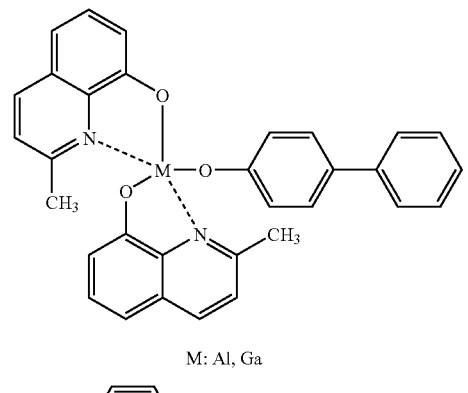
M: Al, Ga
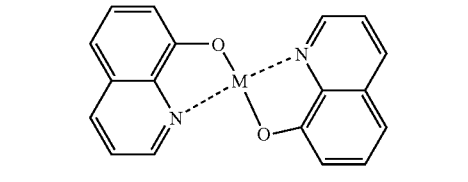
M: Zn, Mg, Be
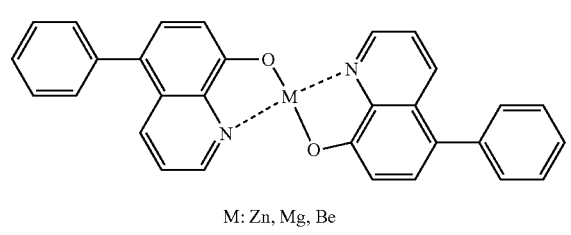
M: Zn, Mg, Be
-continued
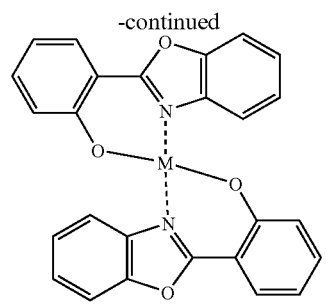
M: Zn, Mg, Be
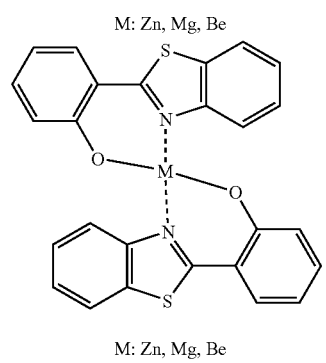
M: Zn, Mg, Be
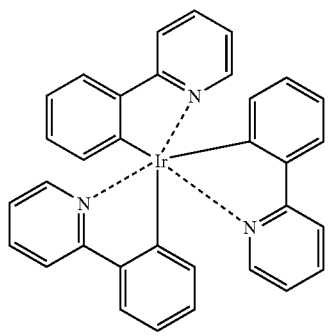
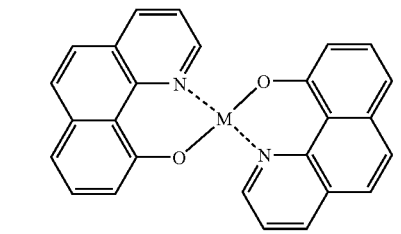
M: Zn, Mg, Be
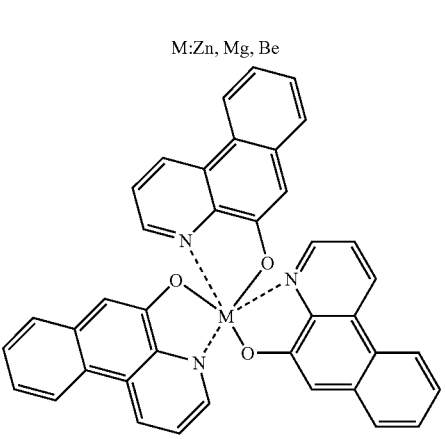
M: Al, Ga Luminescent Material
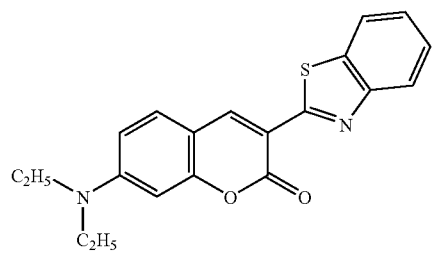
Coumarin6
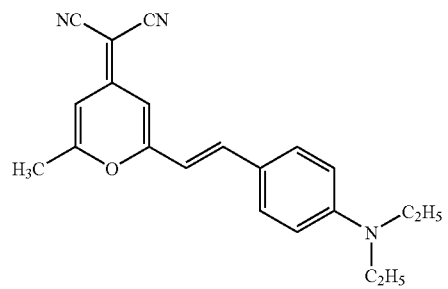
DCM-1
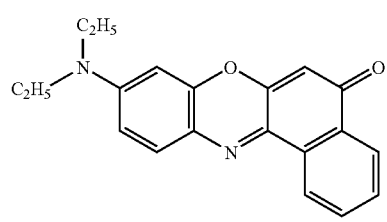
Nile red
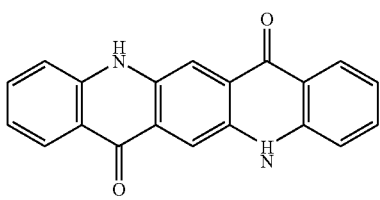
Quinacridone
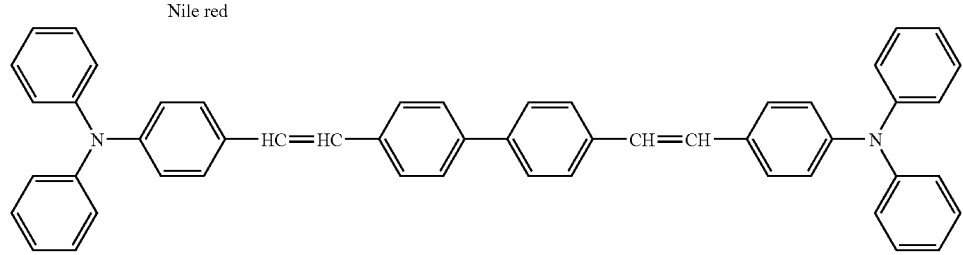
DTPABVI
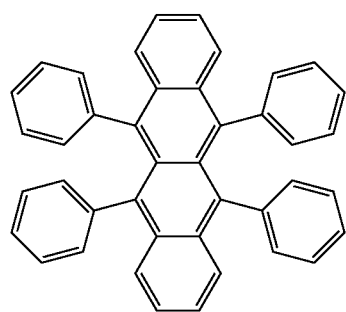
Rubrene
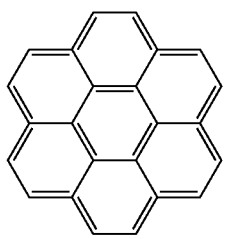
Coronene
Light Emission Layer Matrix Material and Electron-Transporting Material
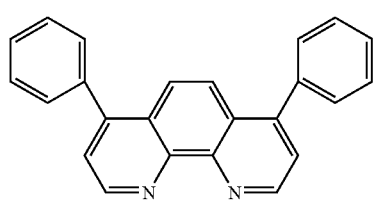
BPhen
-continued
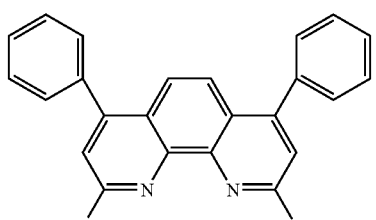
BCP -continued
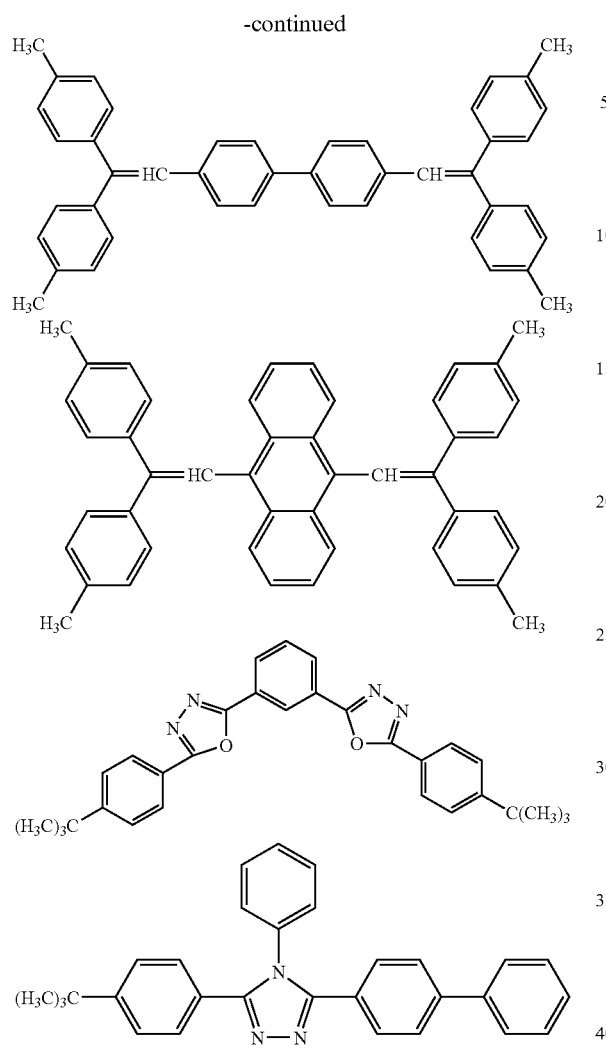
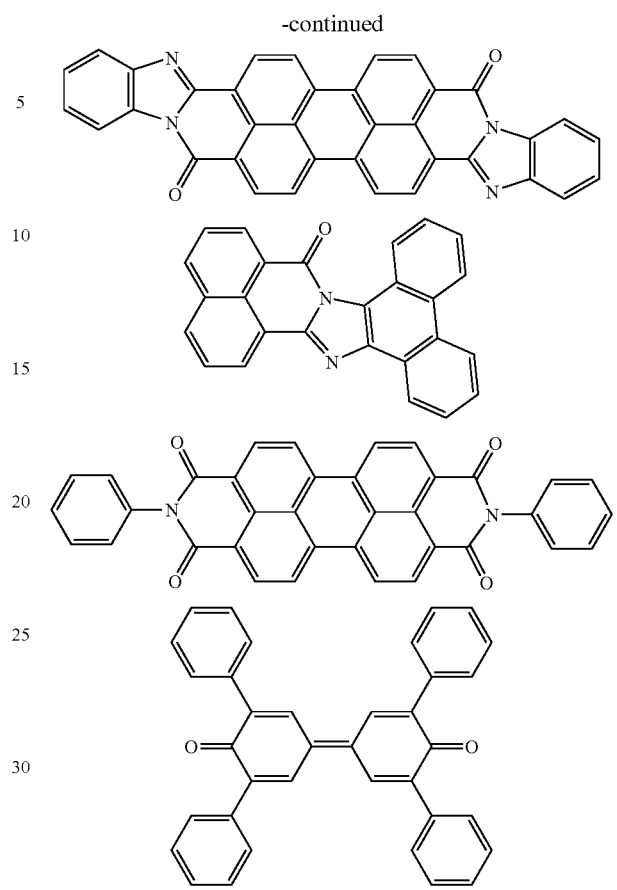
Polymer-Based Hole-Transporting Material
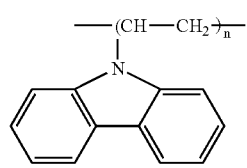
PVCz
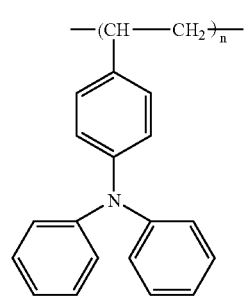
DPA-PS -continued
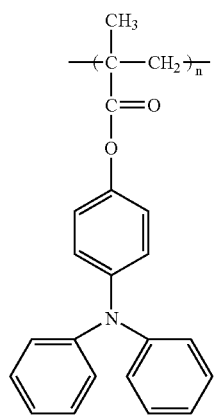
TPA-PMMA
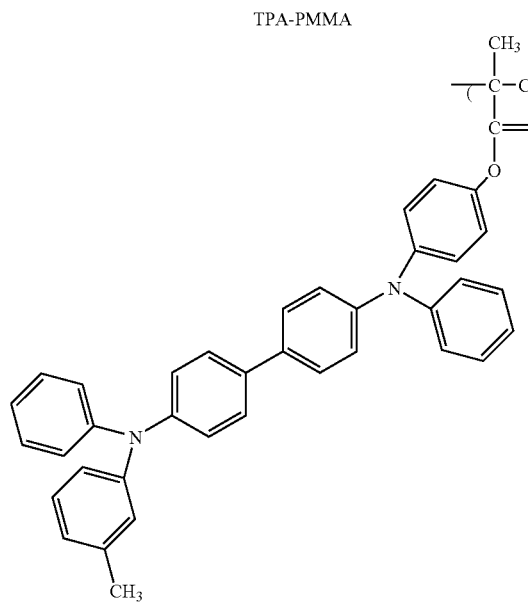
TPD-PMMA
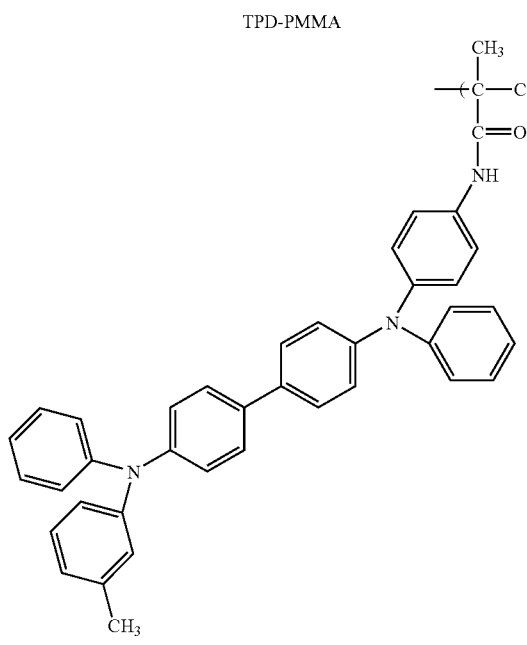
TPD-PMAA -continued

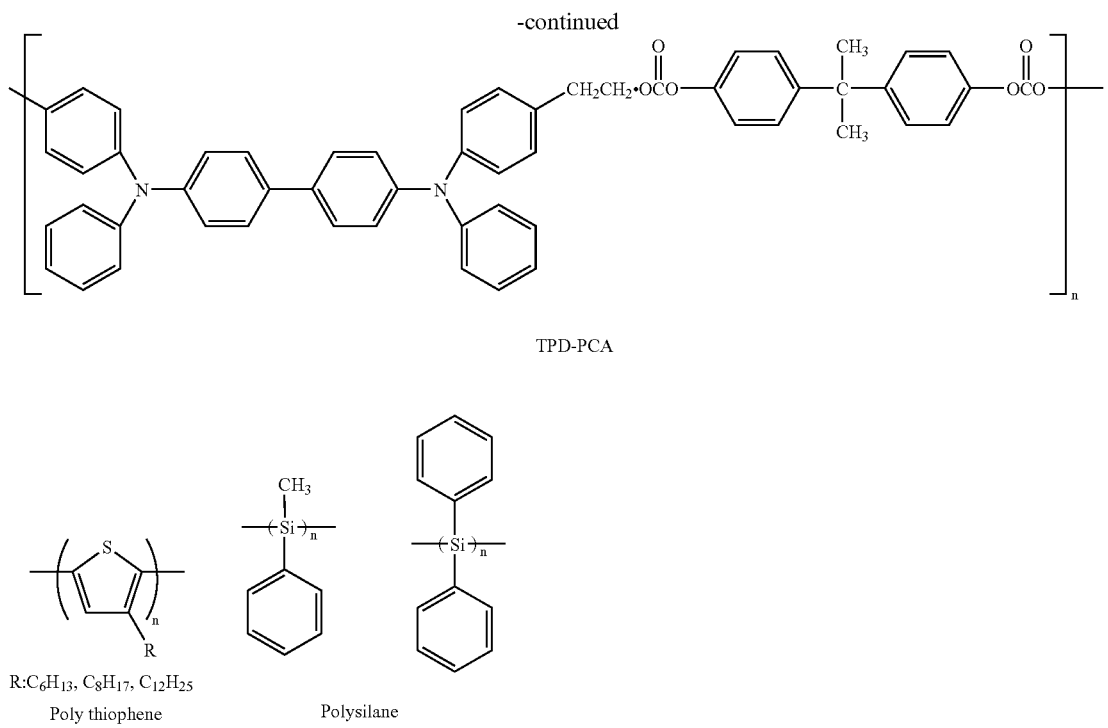

TPD-PCA

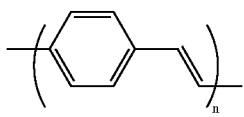

R:C$_6$H$_{13}$, C$_8$H$_{17}$, C$_{12}$H$_{25}$
Poly thiophene          Polysilane Polymer-Based Luminescent Material and Charge-Transporting Material In the organic light-emitting device of the present invention, each of a layer containing the 1,8-naphthyridine compound of the present invention and layers each containing any another organic compound are generally formed into a thin film by means of a vacuum deposition method or an application method involving dissolving the compound into an appropriate solvent. In particular, in the case of film formation by means of the application method, each of the layers can be combined with an appropriate binder resin to form a layer.

The binder resin can be selected from a wide range of binder resins, and examples of the binder resin include, but not limited to, a polyvinyl carbazole resin, a polycarbonate resin, a polyester resin, a polyallylate resin, a polystyrene resin, an acrylic resin, a methacrylic resin, a butyral resin, a polyvinyl acetal resin, a diallyl phthalate resin, a phenol resin, an epoxy resin, a silicone resin, a polysulfone resin, and a urea resin. Each of those binder resins may be used alone, or any one of the binder resins may be mixed with one or two or more other binder resins to be used as a copolymer.

An anode material having as large a work function as possible is desirable. Examples of an anode material that can be used include: metal elements such as gold, silver, platinum, nickel, palladium, cobalt, selenium, and vanadium, and alloys of them; and metal oxides such as tin oxide, zinc oxide, indium tin oxide (ITO), and indium zinc oxide. A conductive polymer such as polyaniline, polypyrrole, polythiophene, or polyphenylene sulfide can also be used. Each of those electrode substances may be used alone, or two or more of them may be used in combination.

On the other hand, a cathode material having as small a work function as possible is desirable. Examples of a cathode material that can be used include metal elements such as lithium, sodium, potassium, cesium, calcium, magnesium, aluminum, indium, silver, lead, tin, and chromium, alloys of two or more of them, and salts of the metal elements. A metal oxide such as indium tin oxide (ITO) can also be used. In addition, a cathode may have a single layer constitution, or may have a multilayer constitution.

A substrate to be used in the present invention is not particularly limited; provided that an opaque substrate such as a metallic substrate or a ceramic substrate, or a transparent substrate such as glass, quartz, or a plastic sheet is used. In addition, a luminescent color can be controlled by using a color filter film, a fluorescent color conversion filter film, a dielectric reflection film, or the like as the substrate.

The produced device may be provided with a protective layer or a sealing layer for the purpose of preventing the device from contacting with oxygen, moisture, or the like. Examples of the protective layer include: inorganic material films such as a diamond thin film, a metal oxide, and a metal nitride; polymer films such as of a fluorine resin, polyparaxylene, polyethylene, a silicone resin, and polystyrene; and a photocurable resin. In addition, the device itself can be covered with glass, a gas impervious film, metal, or the like, and can be packaged with an appropriate sealing resin.

Hereinafter, the present invention will be described more specifically by way of examples. However, the present invention is not limited to the following examples.

Synthesis Example 1

Synthesis of Exemplified Compound No. 6

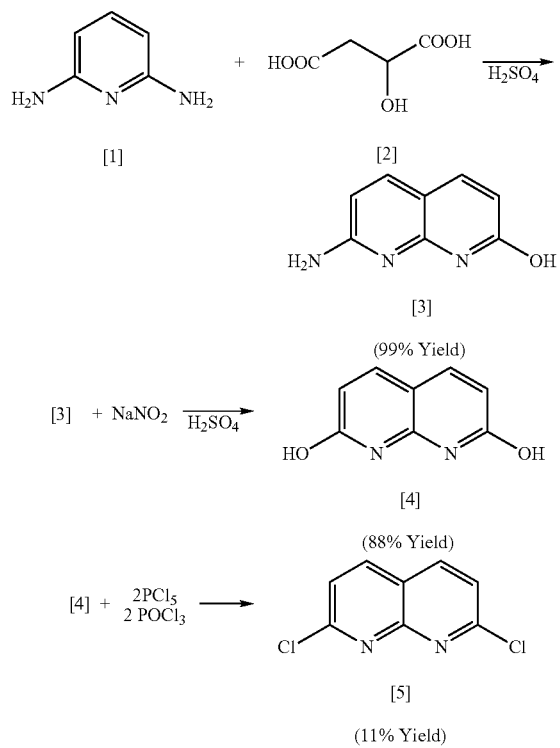

2,7-dichloro-1,8-naphthyridine [5] (white crystal) was obtained from the above compound [1] in a total yield of 9.6% according to the synthesis method described in J. Org. Chem., 46, 833 (1981).

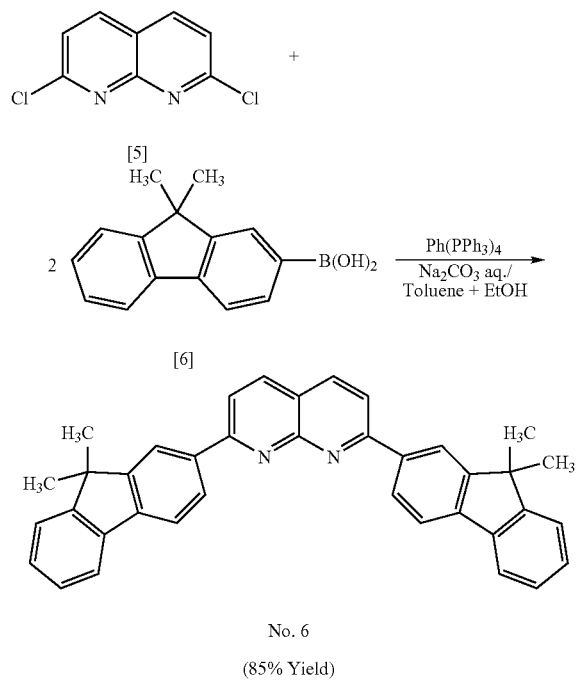

1.0 g (5.78 mmol) of 2,7-dichloro-1,8-naphthyridine [5], 4.1 g (17.3 mmol) of 9,9-dimethylfluorene-2-boronic acid [6], 200 ml of toluene, and 100 ml of ethanol were loaded into a 500-ml three-necked flask. An aqueous solution prepared by dissolving 24 g of sodium carbonate into 120 ml of water was dropped to the mixture while stirring under a nitrogen atmosphere at room temperature. Next, 0.33 g (0.29 mmol) of tetrakis(triphenylphosphine)palladium (0) was added to the mixture. After the mixture had been stirred at room temperature for 30 minutes, the temperature of the mixture was increased to 77° C., and the mixture was stirred for 4 hours. After the reaction, an organic layer was extracted with chloroform, dried with anhydrous sodium sulfate, and purified with a silica gel column (toluene developing solvent), whereby 2.5 g of Exemplified Compound No. 6 (white crystal) were obtained (85% yield).

Synthesis Example 2

Synthesis of Exemplified Compound No. 13

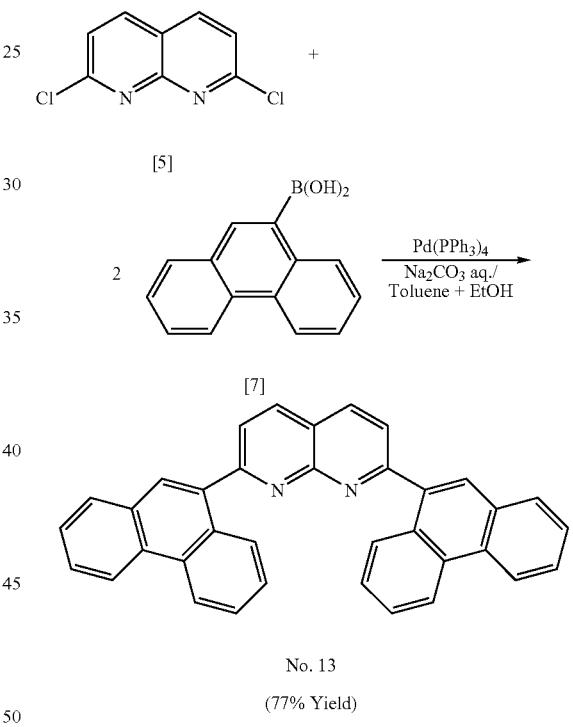

1.0 g (5.78 mmol) of 2,7-dichloro-1,8-naphthyridine [5], 3.2 g (14.5 mmol) of Phenanthene-9-boronic acid [7], 200 ml of toluene, and 100 ml of ethanol were loaded into a 500-ml three-necked flask. An aqueous solution prepared by dissolving 20 g of sodium carbonate into 100 ml of water was dropped to the mixture while stirring under a nitrogen atmosphere at room temperature. Next, 0.33 g (0.29 mmol) of tetrakis(triphenylphosphine)palladium (0) was added to the mixture. After the mixture had been stirred at room temperature for 30 minutes, the temperature of the mixture was increased to 77° C., and the mixture was stirred for 4 hours. After the reaction, an organic layer was extracted with chloroform, dried with anhydrous sodium sulfate, and purified with a silica gel column (mixed developing solvent of toluene and ethyl acetate), whereby 2.1 g of Exemplified Compound No. 13 (white crystal) were obtained (77% yield).

Synthesis Example 3

Synthesis of Exemplified Compound No. 38

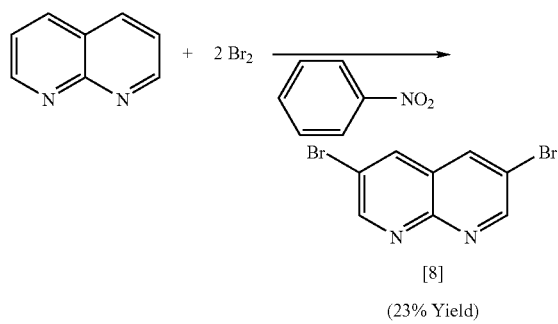

(23% Yield)

3,6-dibromo-1,8-naphthyridine [8] (white crystal) was obtained in a total yield of 23% according to the synthesis method described in J. Heterocyel. Chem., 13, 961 (1976).

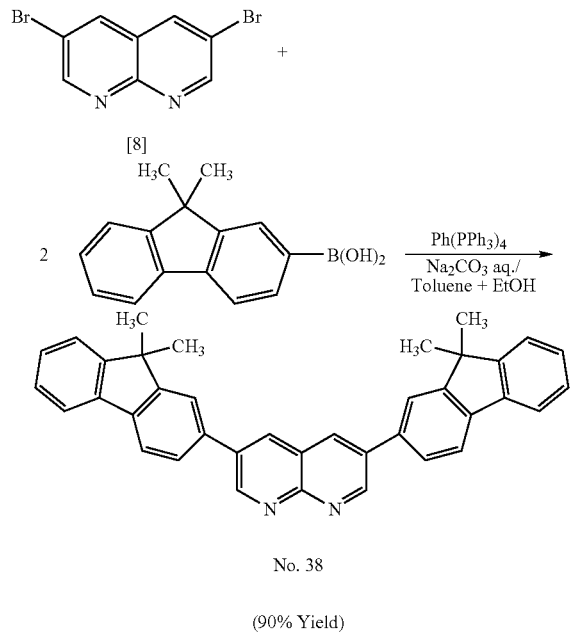

No. 38

(90% Yield)

1.0 g (3.47 mmol) of 3,6-dibromo-1,8-naphthyridine [8], 2.5 g (10.4 mmol) of 9,9-dimethylfluorene-2-boronic acid [6], 200 ml of toluene, and 100 ml of ethanol were loaded into a 500-ml three-necked flask. An aqueous solution prepared by dissolving 20 g of sodium carbonate into 100 ml of water was dropped to the mixture while stirring under a nitrogen atmosphere at room temperature. Next, 0.20 g (0.17 mmol) of tetrakis(triphenylphosphine)palladium (0) was added to the mixture. After the mixture had been stirred at room temperature for 30 minutes, the temperature of the mixture was increased to 77° C., and the mixture was stirred for 4 hours. After the reaction, an organic layer was extracted with chloroform, dried with anhydrous sodium sulfate, and purified with a silica gel column (mixed developing solvent of chloroform and heptane), whereby 1.6 g of Exemplified Compound No. 38 (white crystal) were obtained (90% yield).

Synthesis Example 4

Synthesis of Exemplified Compound No. 49

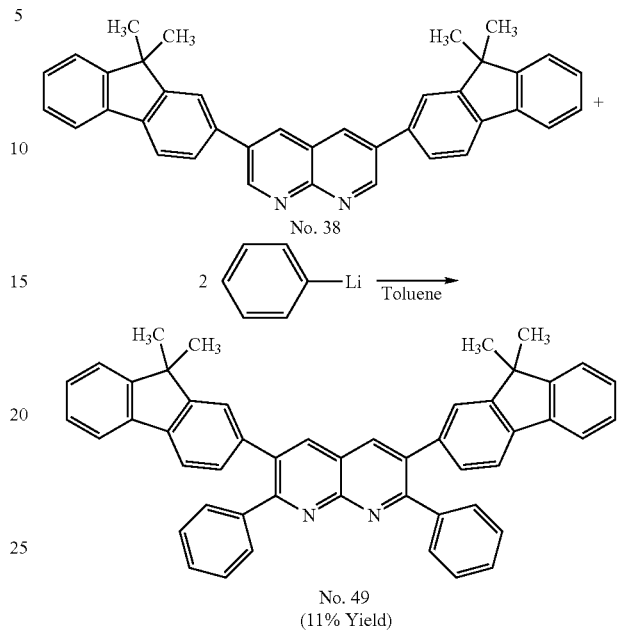

No. 49
(11% Yield)

Synthesis was performed with reference to the synthesis method described in Z. Chem., 18, 382 (1978).

1.0 g (1.94 mmol) of Exemplified Compound No. 38 and 100 ml of toluene were loaded into a 300-ml three-necked flask. 20 ml (19.4 mmol) of a phenyllithium/cyclohexane solution [0.98 mol/l] were dropped to the mixture while stirring under a nitrogen atmosphere at −78° C. After the temperature of the mixture had been gradually increased to room temperature, the mixture was stirred for 8 hours. After the reaction, an organic layer was extracted with chloroform, dried with anhydrous sodium sulfate, and purified with a silica gel column (mixed developing solvent of toluene and ethyl acetate), whereby 0.14 g of Exemplified Compound No. 49 (white crystal) was obtained (11% yield).

Synthesis Example 5

Synthesis of Exemplified Compound No. 57

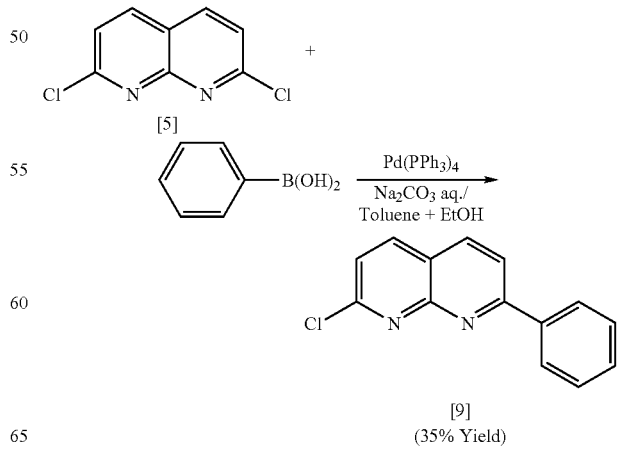

[9]
(35% Yield)

3.0 g (17.3 mmol) of 2,7-dichloro-1,8-naphthyridine [5], 1.6 g (13.0 mmol) of phenyl boronic acid, 200 ml of toluene, and 100 ml of ethanol were loaded into a 500-ml three-necked flask. An aqueous solution prepared by dissolving 24 g of sodium carbonate into 120 ml of water was dropped to the mixture while stirring under a nitrogen atmosphere at room temperature. Next, 1.00 g (0.87 mmol) of tetrakis(triphenylphosphine)palladium (0) was added to the mixture. After the mixture had been stirred at room temperature for 30 minutes, the temperature of the mixture was increased to 77° C., and the mixture was stirred for 1 hours. After the reaction, an organic layer was extracted with chloroform, dried with anhydrous sodium sulfate, and purified with a silica gel column (mixed developing solvent of toluene and ethyl acetate), whereby 1.5 g of 2-chloro-7-Phenyl-1,8-haphthyridine [9] (white crystal) were obtained (35% yield).

1.0 g (4.15 mmol) of 2-chloro-7-phenyl-1,8-naphthyridine [9], 0.47 g (1.04 mmol) of tripinacol [10], 40 ml of toluene, and 20 ml of ethanol were loaded into a 500-ml three-necked flask. An aqueous solution prepared by dissolving 4 g of sodium carbonate into 20 ml of water was dropped to the mixture while stirring under a nitrogen atmosphere at room temperature. Next, 0.17 g (0.15 mmol) of tetrakis(triphenylphosphine)palladium (0) was added to the mixture. After the mixture had been stirred at room temperature for 30 minutes, the temperature of the mixture was increased to 77° C., and the mixture was stirred for 6 hours. After the reaction, an organic layer was extracted with chloroform, dried with anhydrous sodium sulfate, and purified with a silica gel column (mixed developing solvent of toluene and ethyl acetate), whereby 0.50 g of Exemplified Compound No. 57 (yellow crystal) were obtained (73% yield).

Example 1

An organic light-emitting device having the structure shown in FIG. 3 was produced.

Indium tin oxide (ITO) as the anode 2 was formed into a film having a thickness of 120 nm on a glass substrate as the substrate 1 by means of a sputtering method, and the obtained substrate was used as a transparent conductive supporting substrate. The obtained substrate was subjected to ultrasonic cleaning with acetone and isopropyl alcohol (IPA) sequentially, and was then subjected to boiling cleaning with IPA, followed by drying. Furthermore, the transparent conductive supporting substrate was subjected to UV/ozone cleaning before use.

A solution of a compound represented by the following structural formula in chloroform was formed into a film having a thickness of 20 nm on the transparent conductive supporting substrate by means of a spin coating method, whereby the hole transport layer 5 was formed.

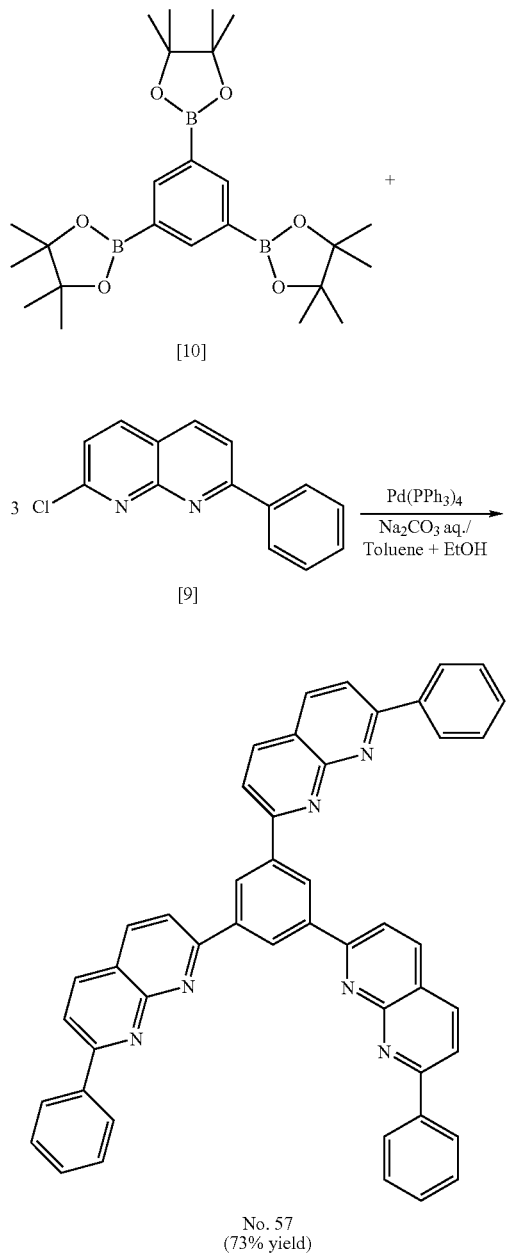

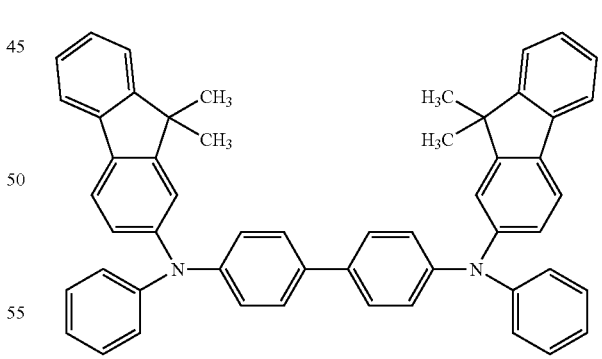

Furthermore, an Ir complex and CBP (at a weight ratio of 5:100) represented by the following structural formulae were formed into a film having a thickness of 20 nm by means of a vacuum deposition method, whereby the light emission layer 3 was formed. Film formation was performed under conditions including: a degree of vacuum upon deposition of $1.0 \times 10^{-4}$ Pa; and a film forming rate of 0.2 to 0.3 nm/sec.

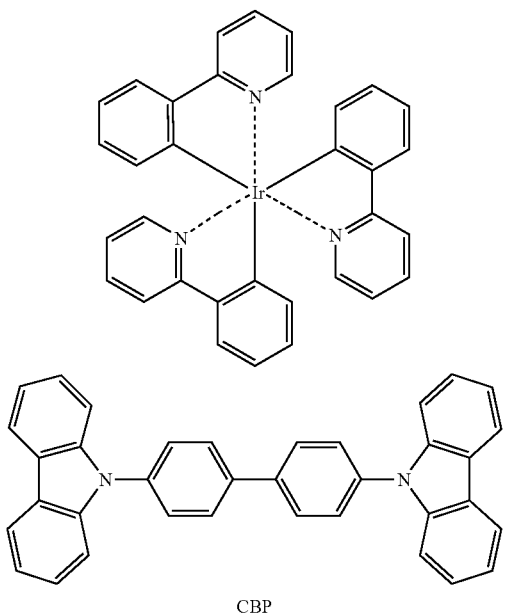

CBP

Furthermore, exemplified compound No. 6 was formed into a film having a thickness of 40 nm by means of a vacuum deposition method, whereby the electron transport layer 6 was formed. Film formation was performed under conditions including: a degree of vacuum upon deposition of $1.0 \times 10^{-4}$ Pa; and a film forming rate of 0.2 to 0.3 nm/sec.

Next, a metal layer film having a thickness of 50 nm as the cathode 4 was formed of a deposition material composed of aluminum and lithium (having a lithium concentration of 1 atomic %) on the organic layer by means of a vacuum deposition method. Furthermore, an aluminum layer having a thickness of 150 nm was formed by means of a vacuum deposition method. Film formation was performed under conditions including: a degree of vacuum upon deposition of $1.0 \times 10^{-4}$ Pa; and a film forming rate of 1.0 to 1.2 nm/sec.

Furthermore, the thus obtained device was covered with a protective glass plate and sealed with an acrylic resin-based adhesive under a nitrogen atmosphere.

A direct voltage of 10 V was applied to the thus obtained device using the ITO electrode (anode 2) as a positive electrode and the Al—Li electrode (cathode 4) as a negative electrode. As a result, a current flowed in the device at a current density of 18 mA/cm$^2$, and green light emission having a luminance of 4,700 cd/m$^2$ was observed.

Furthermore, a voltage was applied for 100 hours with a current density kept at 6.0 mA/cm$^2$. As a result, an initial luminance was 950 cd/m$^2$ was changed to 900 cd/m$^2$ after 100 hours, and luminance degradation was small.

Examples 2 to 23

In each of Examples 2 to 23, an organic light-emitting device was produced in the same manner as in Example 1 except that a compound shown in Table 1 was used instead of Exemplified Compound No. 6, and the device was similarly evaluated. Table 1 also shows the evaluated results.

Comparative Examples 1 to 3

In each of Comparative Examples 1 to 3, an organic light-emitting device was produced in the same manner as in Example 1 except that a compound represented by the following structure formulae was used instead of Exemplified Compound No. 6, and the device was similarly evaluated. Table 1 shows the evaluated results.

Comparative Compound No. 1

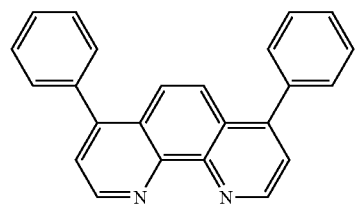

Comparative Compound No. 2

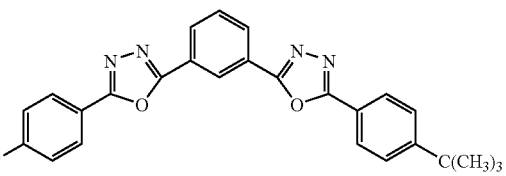

Comparative Compound No. 3

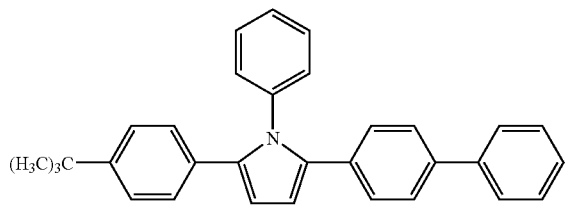

TABLE 1

| Example No. | Exemplified Compound No. | Applied voltage (V) | Initial Luminance (cd/m$^2$) | Current density (mA/cm$^2$) | Initial luminance (cd/m$^2$) | Duration Luminance after 100 hrs. (cd/m$^2$) |
|---|---|---|---|---|---|---|
| Ex. 1 | 6 | 10 | 4700 | 6.0 | 950 | 900 |
| Ex. 2 | 1 | 10 | 4100 | 6.0 | 760 | 660 |

TABLE 1-continued

| Example No. | Exemplified Compound No. | Applied voltage (V) | Initial Luminance (cd/m²) | Duration Current density (mA/cm²) | Initial luminance (cd/m²) | Luminance after 100 hrs. (cd/m²) |
|---|---|---|---|---|---|---|
| Ex. 3 | 5 | 10 | 3900 | 6.0 | 740 | 680 |
| Ex. 4 | 8 | 10 | 4500 | 6.0 | 900 | 860 |
| Ex. 5 | 9 | 10 | 4000 | 6.0 | 800 | 650 |
| Ex. 6 | 20 | 10 | 3800 | 6.0 | 820 | 750 |
| Ex. 7 | 23 | 10 | 4500 | 6.0 | 930 | 820 |
| Ex. 8 | 25 | 10 | 4400 | 6.0 | 840 | 690 |
| Ex. 9 | 27 | 10 | 4600 | 6.0 | 880 | 750 |
| Ex. 10 | 30 | 10 | 4800 | 6.0 | 980 | 890 |
| Ex. 11 | 33 | 10 | 4200 | 6.0 | 850 | 810 |
| Ex. 12 | 36 | 10 | 4000 | 6.0 | 820 | 770 |
| Ex. 13 | 37 | 10 | 3700 | 6.0 | 790 | 670 |
| Ex. 14 | 39 | 10 | 3700 | 6.0 | 830 | 730 |
| Ex. 15 | 40 | 10 | 4000 | 6.0 | 790 | 690 |
| Ex. 16 | 41 | 10 | 3600 | 6.0 | 720 | 640 |
| Ex. 17 | 46 | 10 | 3900 | 6.0 | 800 | 680 |
| Ex. 18 | 48 | 10 | 4700 | 6.0 | 930 | 890 |
| Ex. 19 | 49 | 10 | 4700 | 6.0 | 940 | 890 |
| Ex. 20 | 54 | 10 | 4300 | 6.0 | 900 | 840 |
| Ex. 21 | 55 | 10 | 4400 | 6.0 | 920 | 880 |
| Ex. 22 | 56 | 10 | 4500 | 6.0 | 890 | 860 |
| Ex. 23 | 59 | 10 | 5100 | 6.0 | 990 | 920 |
| Comparative Ex. 1 | Comparative Compound No. 1 | 10 | 3200 | 6.0 | 720 | 350 |
| Comparative Ex. 2 | Comparative Compound No. 2 | 10 | 2300 | 6.0 | 580 | 250 |
| Comparative Ex. 3 | Comparative Compound No. 3 | 10 | 1800 | 6.0 | 530 | 200 |

Example 24

An organic light-emitting device having the structure shown in FIG. 3 was produced.

In the same manner as in Example 1, the hole transport layer 5 was formed on the transparent conductive supporting substrate.

Furthermore, a fluorine compound represented by the following structural formulae was formed into a film having a thickness of 20 nm by means of a vacuum deposition method, whereby the light emission layer 3 was formed. Film formation was performed under conditions including: a degree of vacuum upon deposition of $1.0 \times 10^{-4}$ Pa; and a film forming rate of 0.2 to 0.3 nm/sec.

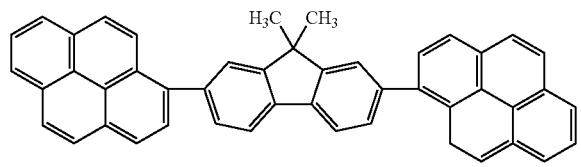

Furthermore, a synthesis of exemplified compound No. 2 was formed into a film having a thickness of 40 nm by means of a vacuum deposition method, whereby the electron transport layer 6 was formed. Film formation was performed under conditions including: a degree of vacuum upon deposition of $1.0 \times 10^{-4}$ Pa; and a film forming rate of 0.2 to 0.3 nm/sec.

Next, the cathode 4 was formed in the same manner as in Example 1, followed by sealing.

A direct voltage of 5 V was applied to the thus obtained device using the ITO electrode (anode 2) as a positive electrode and the Al—Li electrode (cathode 4) as a negative electrode. As a result, a current flowed in the device at a current density of 65 mA/cm², and blue light emission having a luminance of 3,300 cd/m² was observed.

Furthermore, a voltage was applied for 100 hours with a current density kept at 30 mA/cm². As a result, an initial luminance of 1,700 cd/m² was changed to 1,300 cd/m² after 100 hours, and luminance degradation was small.

Examples 25 to 44

In each of Examples 25 to 44, an organic light-emitting device was produced in the same manner as in Example 24 except that a compound shown in Table 2 was used instead of Exemplified Compound No. 2, and the device was similarly evaluated. Table 2 also shows the evaluated results.

Comparative Examples 4 to 6

In each of Comparative Examples 4 to 6, an organic light-emitting device was produced in the same manner as in Example 24 except that a comparative compound No. 1, 2 or 3 was used instead of Exemplified Compound No. 2, and the device was similarly evaluated. Table 2 shows the evaluated results.

TABLE 2

| Example No. | Exemplified Compound No. | Initial Applied voltage (V) | Initial Luminance (cd/m$^2$) | Duration Current density (mA/cm$^2$) | Duration Initial luminance (cd/m$^2$) | Luminance after 100 hrs. (cd/m$^2$) |
|---|---|---|---|---|---|---|
| Ex. 24 | 2 | 5 | 3300 | 30 | 1700 | 1300 |
| Ex. 25 | 4 | 5 | 3100 | 30 | 1400 | 1100 |
| Ex. 26 | 6 | 5 | 3500 | 30 | 1900 | 1500 |
| Ex. 27 | 7 | 5 | 3000 | 30 | 1400 | 1000 |
| Ex. 28 | 10 | 5 | 2700 | 30 | 900 | 650 |
| Ex. 29 | 13 | 5 | 3500 | 30 | 1700 | 1400 |
| Ex. 30 | 24 | 5 | 3400 | 30 | 1600 | 1100 |
| Ex. 31 | 26 | 5 | 3400 | 30 | 1800 | 1200 |
| Ex. 32 | 28 | 5 | 3300 | 30 | 1600 | 1300 |
| Ex. 33 | 29 | 5 | 3100 | 30 | 1300 | 950 |
| Ex. 34 | 31 | 5 | 3100 | 30 | 1200 | 850 |
| Ex. 35 | 32 | 5 | 2900 | 30 | 1300 | 1000 |
| Ex. 36 | 34 | 5 | 2800 | 30 | 950 | 750 |
| Ex. 37 | 38 | 5 | 2700 | 30 | 1000 | 700 |
| Ex. 38 | 45 | 5 | 2800 | 30 | 1000 | 750 |
| Ex. 39 | 47 | 5 | 3200 | 30 | 1300 | 1000 |
| Ex. 40 | 51 | 5 | 3200 | 30 | 1100 | 850 |
| Ex. 41 | 53 | 5 | 2800 | 30 | 950 | 800 |
| Ex. 42 | 57 | 5 | 3300 | 30 | 1500 | 1300 |
| Ex. 43 | 58 | 5 | 3200 | 30 | 1600 | 1300 |
| Ex. 44 | 60 | 5 | 3000 | 30 | 1200 | 850 |
| Comparative Ex. 4 | Comparative Compound No. 1 | 5 | 2400 | 30 | 750 | 400 |
| Comparative Ex. 5 | Comparative Compound No. 2 | 5 | 1300 | 30 | 550 | 200 |
| Comparative Ex. 6 | Comparative Compound No. 3 | 5 | 900 | 30 | 500 | 200 |

Example 45

An organic light-emitting device having the structure shown in FIG. 2 was produced.

In the same manner as in Example 1, the hole transport layer 5 was formed on the transparent conductive supporting substrate.

Furthermore, exemplified compound No. 3 was formed into a film having a thickness of 40 nm by means of a vacuum deposition method to form the electron transport layer 6 also serving as the light emission layer. Film formation was performed under conditions including: a degree of vacuum upon deposition of $1.0 \times 10^{-4}$ Pa; and a film forming rate of 0.2 to 0.3 nm/sec.

Next, the cathode 4 was formed in the same manner as in Example 1, followed by sealing.

A direct voltage of 5 V was applied to the thus obtained device using the ITO electrode (anode 2) as a positive electrode and the Al—Li electrode (cathode 4) as a negative electrode. As a result, a current flowed in the device at a current density of 45 mA/cm$^2$, and blue light emission having a luminance of 1,800 cd/m$^2$ was observed.

Furthermore, a voltage was applied for 100 hours with a current density kept at 30 mA/cm$^2$. As a result, an initial luminance was 1100 cd/m$^2$ was changed to 750 cd/m$^2$ after 100 hours, and luminance degradation was small.

Examples 46 to 61

In each of Examples 46 to 61, an organic light-emitting device was produced in the same manner as in Example 45 except that a compound shown in Table 3 was used instead of Exemplified Compound No. 3, and the device was similarly evaluated. Table 3 also shows the evaluated results.

Comparative Examples 7 to 9

In each of Comparative Examples 7 to 9, a light-emitting device was produced in the same manner as in Example 45 except that a comparative compound No 1, 2 or 3 was used instead of Exemplified Compound No. 3, and the device was similarly evaluated. Table 3 shows the evaluated results.

TABLE 3

| Example No. | Exemplified Compound No. | Initial | | Duration | | Luminance after 100 hrs. (cd/m$^2$) |
|---|---|---|---|---|---|---|
| | | Applied voltage (V) | Luminance (cd/m$^2$) | Current density (mA/cm$^2$) | Initial luminance (cd/m$^2$) | |
| Ex. 45 | 3 | 5 | 1800 | 30 | 1100 | 750 |
| Ex. 46 | 11 | 5 | 2000 | 30 | 1200 | 850 |
| Ex. 47 | 12 | 5 | 1700 | 30 | 900 | 650 |
| Ex. 48 | 14 | 5 | 2200 | 30 | 1400 | 1100 |
| Ex. 49 | 15 | 5 | 2000 | 30 | 1000 | 800 |
| Ex. 50 | 16 | 5 | 1500 | 30 | 750 | 550 |
| Ex. 51 | 17 | 5 | 1400 | 30 | 700 | 500 |
| Ex. 52 | 18 | 5 | 2100 | 30 | 1400 | 1000 |
| Ex. 53 | 19 | 5 | 1600 | 30 | 900 | 650 |
| Ex. 54 | 21 | 5 | 1600 | 30 | 1000 | 750 |
| Ex. 55 | 22 | 5 | 1500 | 30 | 1000 | 700 |
| Ex. 56 | 35 | 5 | 1300 | 30 | 700 | 550 |
| Ex. 57 | 42 | 5 | 1900 | 30 | 1200 | 850 |
| Ex. 58 | 43 | 5 | 1700 | 30 | 900 | 650 |
| Ex. 59 | 44 | 5 | 1800 | 30 | 1000 | 700 |
| Ex. 60 | 50 | 5 | 2000 | 30 | 1200 | 950 |
| Ex. 61 | 52 | 5 | 2300 | 30 | 1400 | 1100 |
| Comparative Ex. 7 | Comparative Compound No. 1 | 5 | 350 | 30 | 250 | 100 |
| Comparative Ex. 8 | Comparative Compound No. 2 | 5 | 200 | 30 | 150 | No light emission |
| Comparative Ex. 9 | Comparative Compound No. 3 | 5 | 250 | 30 | 150 | No light emission |

This application claims priority from Japanese Patent Application No. 2005-180391 filed on Jun. 21, 2005, which is hereby incorporated by reference herein.

What is claimed is:

1. A compound represented by the following formula:

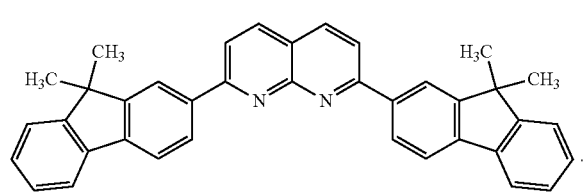

2. An organic light-emitting device comprising:
a pair of electrodes; and
an organic compound layer provided between the pair of electrodes,
wherein the organic compound layer comprises the compound according to claim 1.

3. The organic light-emitting device according to claim 2, wherein the organic light-emitting device further comprises a light emission layer which is in contact with the organic compound layer, and wherein the pair of electrodes is an anode and a cathode and the organic compound layer is provided between the light emission layer and the cathode.

4. The organic light-emitting device according to claim 3, wherein the organic compound layer is an electron transport layer.

5. The organic light-emitting device according to claim 3, wherein the light-emitting device emits green color.

6. A compound represented by the following formula:

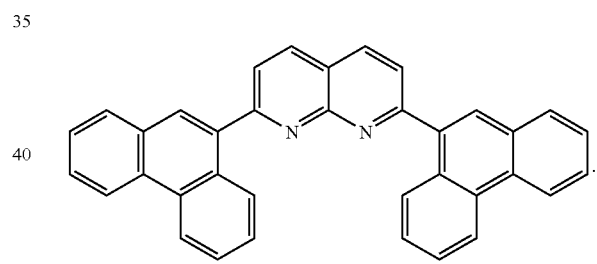

7. An organic light-emitting device comprising:
a pair of electrodes; and
an organic compound layer provided between the pair of electrodes,
wherein the organic compound layer comprises the compound according to claim 6.

8. The organic light-emitting device according to claim 7, wherein the organic light-emitting device further comprises a light emission layer which is in contact with the organic compound layer, and wherein the pair of electrodes is an anode and a cathode and the organic compound layer is provided between the light emission layer and the cathode.

9. The organic light-emitting device according to claim 8, wherein the organic compound layer is an electron transport layer.

10. The organic light-emitting device according to claim 8, wherein the light-emitting device emits blue color.

* * * * *